(12) United States Patent
Lorenzo et al.

(10) Patent No.: US 9,901,254 B2
(45) Date of Patent: *Feb. 27, 2018

(54) SYSTEMS AND METHODS FOR VIRTUAL INDEX-MATCHING OF DIFFUSIVE MEDIA

(71) Applicant: VisEn Medical, Inc., Waltham, MA (US)

(72) Inventors: Jorge Ripoll Lorenzo, Zurich (CH); Wael I. Yared, Lexington, MA (US); Joshua Kempner, Reading, MA (US)

(73) Assignee: VisEn Medical, Inc., Waltham, MA (US)

( * ) Notice: Subject to any disclaimer, the term of this patent is extended or adjusted under 35 U.S.C. 154(b) by 836 days.

This patent is subject to a terminal disclaimer.

(21) Appl. No.: 13/801,763

(22) Filed: Mar. 13, 2013

(65) Prior Publication Data

US 2013/0281842 A1    Oct. 24, 2013

Related U.S. Application Data

(63) Continuation of application No. 12/888,075, filed on Sep. 22, 2010, now Pat. No. 8,401,619.
(Continued)

(51) Int. Cl.
*A61B 5/05*   (2006.01)
*A61B 5/00*   (2006.01)
(Continued)

(52) U.S. Cl.
CPC ....... *A61B 5/0073* (2013.01); *G01N 21/6456* (2013.01); *G01N 21/6486* (2013.01);
(Continued)

(58) Field of Classification Search
CPC ............................... A61B 6/032; A61B 6/504
See application file for complete search history.

(56) References Cited

U.S. PATENT DOCUMENTS

| 4,981,977 A | 1/1991 | Southwick et al. |
| 5,268,486 A | 12/1993 | Waggoner et al. |

(Continued)

FOREIGN PATENT DOCUMENTS

| CN | 101057788 A | 10/2007 |
| EP | 1065250 A1 | 1/2001 |

(Continued)

OTHER PUBLICATIONS

Achilefu et al. (2000) "Novel Receptor-Targeted Fluorescent Contract Agents for In Vivo Tumor Imaging," Invest. Radiol. 35:479-485.
(Continued)

*Primary Examiner* — Hien Nguyen
(74) *Attorney, Agent, or Firm* — Choate, Hall & Stewart LLP; William R. Haulbrook; Ronen Adato

(57) ABSTRACT

The invention relates to systems and methods for tomographic imaging of a subject comprising diffuse media by converting measurements of electromagnetic radiation, e.g., fluorescent light, obtained in free space exterior to the subject into data that would be measured if the subject were surrounded by an infinite and homogeneous diffusive medium, e.g., a medium with optical properties equal to the average optical properties of the subject. After applying a transformation to convert measurements to virtually-matched values, propagation of light is simulated from the index-matched surface to a set of virtual detectors exterior to the subject and arranged in a geometrically advantageous fashion, for example, in a planar array, thereby facilitating the use of fast reconstruction techniques.

46 Claims, 9 Drawing Sheets

Related U.S. Application Data

(60) Provisional application No. 61/244,674, filed on Sep. 22, 2009.

(51) Int. Cl.
  *G01N 21/64* (2006.01)
  *G01N 21/17* (2006.01)
  *A61B 6/03* (2006.01)

(52) U.S. Cl.
  CPC ......... *A61B 6/037* (2013.01); *A61B 2562/146* (2013.01); *G01N 2021/1787* (2013.01)

(56) References Cited

U.S. PATENT DOCUMENTS

| | | |
|---|---|---|
| 5,486,616 A | 1/1996 | Waggoner et al. |
| 5,569,587 A | 10/1996 | Waggoner |
| 5,569,766 A | 10/1996 | Waggoner et al. |
| 5,627,027 A | 5/1997 | Waggoner |
| 5,808,044 A | 9/1998 | Brush et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,133,445 A | 10/2000 | Waggoner et al. |
| 6,136,612 A | 10/2000 | Della Ciana et al. |
| 6,448,008 B1 | 9/2002 | Caputo et al. |
| 6,534,041 B1 | 3/2003 | Licha et al. |
| 6,615,063 B1 | 9/2003 | Ntziachristos et al. |
| 6,747,159 B2 | 6/2004 | Caputo et al. |
| 7,383,076 B2 | 6/2008 | Ntziachristos et al. |
| 7,445,767 B2 | 11/2008 | Licha et al. |
| 7,473,415 B2 | 1/2009 | Kawakami et al. |
| 7,488,468 B1 | 2/2009 | Miwa et al. |
| 7,547,721 B1 | 6/2009 | Miwa et al. |
| 7,647,091 B2 | 1/2010 | Ntziachristos et al. |
| 7,804,075 B2 | 9/2010 | Ntziachristos et al. |
| 7,962,200 B2 | 6/2011 | Ntziachristos et al. |
| 8,401,618 B2 | 3/2013 | Lorenzo et al. |
| 8,401,619 B2 | 3/2013 | Lorenzo et al. |
| 2005/0283071 A1* | 12/2005 | Ripoll et al. .................. 600/425 |
| 2009/0131800 A1 | 5/2009 | Liang |
| 2009/0240138 A1 | 9/2009 | Yi |

FOREIGN PATENT DOCUMENTS

| | | |
|---|---|---|
| EP | 1113822 A1 | 7/2001 |
| EP | 1181940 B1 | 12/2004 |
| EP | 1480683 A2 | 12/2004 |
| EP | 1679082 A1 | 7/2006 |
| EP | 0988060 B1 | 6/2007 |
| GR | 1005346 B1 | 11/2006 |
| WO | WO-96/17628 A1 | 6/1996 |
| WO | WO-97/40104 A1 | 10/1997 |
| WO | WO-98/47538 A2 | 10/1998 |
| WO | WO-99/51702 A1 | 10/1999 |
| WO | WO-00/16810 A1 | 3/2000 |
| WO | WO-01/21624 A1 | 3/2001 |
| WO | WO-01/43781 A1 | 6/2001 |
| WO | WO-02/41760 A2 | 5/2002 |
| WO | WO-03/074091 A2 | 9/2003 |
| WO | WO-2004/072906 A1 | 8/2004 |
| WO | WO-2006072580 A1 | 7/2006 |
| WO | WO-2007/072085 A1 | 6/2007 |
| WO | WO-2009/055095 A1 | 4/2009 |

OTHER PUBLICATIONS

Ai et al. (2007) "Exploration of New Chromophore Structures Leads to the Identification of Improved Blue Fluorescent Proteins," Biochemistry 46:5904-5910.

Aronson, R. (1995) "Boundary conditions for diffusion of light," J. Opt. Soc. Am. A 12:2532.

Arridge et al. (2000) "The finite element model for the propagation of light in scattering media: a direct method for domains with nonscattering regions." Med. Phys. 27(1):252-264.

Australian Patent Examination Report, Application No. 2010298388, Nov. 7, 2013, 2 pages.

Baird et al. (2000) "Biochemistry, mutagenesis, and oligomerization of DsRed, a red fluorescent protein from coral," Proc. Nat. Acad. Sci. 97:11984-11989.

Ballou et al. (1997) "Tumor Detection and Visualization Using Cynanine Fluorochrome-Labeled Antibodies," Biotechnol. Prog. 13:649:658.

Becker et al. (2001) "Receptor-targeted optical imaging of tumors with near-infrared fluorescent ligands," Nature Biotech. 19:327-331.

Bremer et al. (2001) "In Vivo molecular target assessment of matrix metalloproteinase inhibition," Nature Med. 7:743-748.

Bugaj et al. (2001) "Novel fluorescent contrast agents for optical imaging of in vivo tumors based on a receptor-targeted dye-peptide conjugate platform," J. Biomed. Opt. 6:122-133.

Campbell et al. (2002) "A monomeric red fluorescent protein," Proc. Nat. Acad. Sci. 96:7877-7882.

Campo et al. (2007) "Polymeric Photosensitizer Prodrugs for Photodynamic Therapy," Photochem. Photobiol. 83:958-965.

Cubitt et al. (1995) "Understanding, improving and using green fluorescent proteins" Trends Biochem Sci. 11:448-455.

European Official Action, Application No. 10 776 206.4, Mar. 25, 2013, 3 pages.

Giepmans et al. (2006) "The Fluorescent Toolbox for Assessing Protein Location and Function," Science 312:217-224.

Heikal et al. (2000) "Mollecular spectroscopy and dynamics of intrinsically fluorescent proteins: coral red (dsRed) and yellow (Citrine)," Proc. Nat. Acad. Sci. 97:11996-12001.

Heim et al. (1994) "Wavelength mutations and prostranslational autoxidation of green fluorescent protein," Proc. Nat. Acad. Sci. 91:12501-12504.

Heim et al. (1996) "Engineering green fluorescent protein for improved brightness, longer wavelengths and fluorescence resonance energy transfer," Curr. Biol. 6:178-182.

Hielscher et al. (1998) "Comparison of finite-difference transport and iffusion calculations for photon migration in homogenous and heterogeneous tissues." Phys. Med. Biol. 43:1285-1302.

International Preliminary Report on Patentability, PCT/US2010/049831, Mar. 27, 2012.

International Search Report for PCT/US2010/049831 dated Feb. 15, 2011, 5 pages.

Jorge Ripoll et al., Noncontact Diffuse Optical Tomography, Proc. SPIE 5474, vol. 5474, Sep. 2, 2004.

Lackowicz (1999) "Principals of Fluorescence Spectroscopy," 2nd Ed., Kluwar Academic, New York, pp. 87-88.

Markel et al. (2001) Inverse scattering for the diffusion equation with general boundary conditions. Phys. Rev. E. 64(3 Pt 2):035601.

Markel et al. (2004) "Symmetries, inversion formulas, and image reconstruction for optical tomography." Phys. Rev. E Stat Nonlin Soft Mater Phys. 70(5 Pt 2):056616.

Neri et al. (1997)"Targeting by affinity-matured recombinant antibody fragments of an angiogenesis associated fibronectin isoform," Nature Biotech. 15:1271-1275.

Ntziachristos et al. (2001) "Experimental three-dimensional fluorescence reconstruction of diffuse media using a normalized Born approximation." Opt. Lett. 26(12):893-895.

Ntziachristos et al. (2004) "Fluorescence molecular tomography: new detection schemes for acquiring high information content measurements," Biomedical Imaging: Macro to Nano, IEEE Int'l. Symposium on Apr. 15, 2004 pp. 1475-1478.

Ntziachristos et al. (2005) "Looking and listening to Light: the evolution of whole-body photonic imaging." Nat. Biotechnol. 23(3):313-320.

Ntziachristos et al., Fluorescence Molecular Tomography: New Detection Schemes for Acquiring High Information Content Measurements, BioMedical Imaging: Macro to Nano, IEEE International Symposium on Arlington, VA, USA Apr. 15, 2004.

(56) References Cited

OTHER PUBLICATIONS

Ozmen et al (2000) "Infrared fluorescence sensing of submicromolar calcium: pushing the limits of photoinduced electron transfer" Tetrahedron Letters 9185-9188.

Ripoll et al. (1999) "Scattering integral equations for diffusive waves: detection of objects buried in diffusive media in the presence of rough interfaces," J. Opt. Soc. Am. A 16:1453-1465.

Ripoll et al. (2001) "The Kirchhoff Approximation for diffusive waves." Phys. Rev. E. 64:051917:1-8.

Ripoll et al. (2002) "Fast analytical approximation for arbitrary geometries in diffuse optical tomography." Opt. Let. 27(7):527-529.

Ripoll et al. (2003) "Iterative boundary method for diffuse optical tomography." J. Opt. Soc. Am. A 20(6):1103-1110.

Ripoll et al. (2004) "Noncontact diffuse optical tomography," Proc. Spie 5474:215-223.

Ripoll et al. (2005) "Experimental determination of photon propagation in highly absorbing and scattering media." J. Opt. Soc. Am. A:22(3):546-551.

Ripoll et al. (2006) "From finite to infinite volumes: removal of boundaries in diffuse wave imaging." Phys. Rev. Lett. 96:173903.

Shaner et al. (2004) "Improved monomeric red, orange and yellow fluorescent proteins derived from Discoma sp red fluorescent protein," Nat. Biotech 22:1567-1572.

Shaner et al. (2005) "A Guide to Choosing Fluorescent Proteins," Nature Methods 2:905-909.

Tsien (1998) "The green fluorescent protein," Ann. Rev. Biochem. 67:509-544.

Tyagi et al. (1998) "Multicolor molecular beacons for allele discrimination," Nat. Biotechnol. 16:49-53.

Tyagi et al. (2000) "Wavelength-shifting molecular beacons," Nat. Biotechnol. 18:1191-1196.

Weissleder et al. (1999) "In vivo imaging of tumors with protease-activated hear-infrared fluorescent probes," Nature Biotech. 17:375-378.

Written Opinion for PCT/US2010/049831 dated Feb. 15, 2011, 7 pages.

Zhang et al. (2002) "Creating new fluorescent probes for cell biology," Nat. Rev. Mol. Biol. 3:906-918.

\* cited by examiner

SYSTEMS AND METHODS FOR VIRTUAL INDEX-MATCHING OF DIFFUSIVE MEDIA

RELATED APPLICATION APPLICATIONS

This application claims priority to and the benefit of, U.S. patent application Ser. No. 12/888,075, which was filed on Sep. 22, 2010 and claims priority to U.S. Provisional Patent Application No. 61/244,674, which was filed on Sep. 22, 2009, each of which are herein incorporated by reference in their entireties.

RELATED APPLICATION

This application claims priority to and the benefit of, and incorporates herein by reference in its entirety, U.S. Provisional Patent Application No. 61/244,674, which was filed on Sep. 22, 2009.

FIELD OF THE INVENTION

The invention relates generally to in vivo imaging systems and methods. More particularly, in certain embodiments, the invention relates to a tomographic imaging system employing a virtual index matching technique.

BACKGROUND OF THE INVENTION

Tomography is based on utilizing data sets to obtain images or infer the optical properties of the medium under study. Many different numerical and analytical approaches have been developed for modeling photon propagation and effectively provide the solutions necessary for tomographic inversion of the data sets collected. This has grown into an active field (see, e.g., Ntziachristos, Ripoll et al. (2005) "Looking and listening to light: the evolution of whole-body photonic imaging." Nat. Biotechnol. 23 (3): 313-320 and Arridge, Dehghani et al. (2000) "The finite element model for the propagation of light in scattering media: a direct method for domains with nonscattering regions." Med. Phys. 27(1):252-264 for reviews). For the most general case of imaging a subject with arbitrary geometries, numerical techniques are most pertinent. In all these numerical methods, the objective is to determine the distribution of luminescent or fluorescent sources inside a heterogeneous or homogeneous medium from a relatively small number of surface measurements (in the order of $10^2$-$10^3$). With improvements in detector technology and computational platforms, higher numbers of measurements have become possible, which has led to new numerical methods that can deal with such large data sets. These techniques have been developed so as to reduce the memory and computing time needed to solve for such large systems of equations (see, e.g., Ripoll, Ntziachristos et al. (2001) "The Kirchhoff Approximation for diffusive waves." Phys. Rev. E. 64: 051917:1-8; Ripoll, Nieto-Vesperinas et al. (2002) "Fast analytical approximation for arbitrary geometries in diffuse optical tomography." Opt. Let. 27(7): 527-529; and Markel and Schotland (2004) "Symmetries, inversion formulas, and image reconstruction for optical tomography." Phys. Rev. E Stat Nonlin Soft Matter Phys. 70(5 Pt 2): 056616). At present, however, a point has been reached where a compromise is needed when dealing with arbitrary geometries: either accurate methods are used by reducing considerably the size of the data sets (see, e.g., Hielscher, Alcouffe et al. (1998) "Comparison of finite-difference transport and diffusion calculations for photon migration in homogenous and heterogeneous tissues." Phys. Med. Biol. 43: 1285-1302 and Arridge, Dehghani et al. (2000) "The finite element model for the propagation of light in scattering media: a direct method for domains with nonscattering regions." Med. Phys. 27(1):252-264), or approximate methods are employed to speed up calculations at the expense of the accuracy of the result (see, e.g., Ripoll, Ntziachristos et al. (2001) "The Kirchhoff Approximation for diffusive waves." Phys. Rev. E. 64: 051917:1-8).

SUMMARY OF THE INVENTION

The invention relates to systems and methods for tomographic imaging of a diffuse subject by converting measurements of electromagnetic radiation (e.g., fluorescent light) obtained in free space, exterior to the subject, into data that would be measured if the subject were surrounded by an infinite and homogeneous diffusive medium, e.g., a medium with optical properties equal to the average optical properties of the subject. After applying a transformation to convert measurements to virtually-matched values, propagation of light is simulated from the index-matched surface to a set of virtual detectors exterior to the subject and arranged in a geometrically advantageous fashion, for example, in a planar array, thereby facilitating the use of fast reconstruction techniques. In particular embodiments, the invention features methods of fluorescence molecular tomographic (FMT) reconstruction in vivo of signals, reporters and/or agents (i.e., contrast agents or probes) in a diffusive medium (e.g., a mammalian subject). The method preserves the three-dimensional fluorophore distribution and quantitative nature of the FMT approach while substantially accelerating its computation speed and simplifying the underlying equations.

In preferred embodiments, systems and methods of the invention transform fluorescence measurements to those that would be obtained if the surrounding non-diffusive medium were filled with a diffusive medium with the same optical properties as those of the object. This situation would then correspond to the case where the original diffusive volume is infinite and homogeneous. This technique has two important consequences. First, it allows the use of infinite homogeneous functions (e.g., Green's functions) to generate analytical forward solutions for the inverse problem, thereby avoiding the use of complex numerical methods which solve for arbitrary geometries. This has a direct impact in significantly accelerating the computation for tomographic images. Second, this technique allows for propagating the data to virtual detectors located anywhere outside the volume, thereby facilitating the conformation of detector areas to any general shape, in particular to a planar array of detectors. This enables the use of exact inversion methods such as those proposed in Markel and Schotland (2001) "Inverse scattering for the diffusion equation with general boundary conditions." Phys. Rev. E. 64(3 Pt 2): 035601 and Markel and Schotland (2004) "Symmetries, inversion formulas, and image reconstruction for optical tomography." Phys. Rev. E Stat Nonlin Soft Matter Phys. 70(5 Pt 2): 056616) and the application of fast reconstruction methods such as the Hybrid approach (see, e.g., U.S. patent application Ser. No. 12/870,454, "Systems and Methods for Tomographic Imaging in Diffuse Media using a Hybrid Inversion Technique," by Ripoll Lorenzo et al.).

Furthermore, once outside the diffusive volume, data can be back-propagated inside the diffusive volume, a transformation which is not possible in the presence of arbitrary interfaces. The technique can be used, for example, to recover the spatial distribution and concentration of fluorescent signatures in an arbitrary geometry by virtually index-matching the surface measurements and using the normalized Born approximation (see, e.g., U.S. Pat. Nos. 6,615,063 and 7,383,076, both entitled "Fluorescence-Mediated Molecular Tomography," and International Patent Application No. PCT/US2008/65648, entitled, "Imaging Systems Featuring Waveguiding Compensation").

Embodiments of the present invention can be used in combination with various solutions of the diffuse problem, including numerical and/or analytical solutions of the transport equation, or its derivations and approximations such as the Boltzmann Equation or the Diffusion Equation. As such, certain embodiments of this invention can also be used for resolving absorption, scattering or fluorescence contrast and in combination with contrast agents and molecular probes. The index matching techniques described herein are applicable where the diffusion regime dominates. Hence, the techniques are applicable not only to light diffusion but also to electron and neutron diffusion and any other diffusive process such as electromagnetic propagation of all wavelengths in highly scattering media such as microwave scattering from random scatterers, or sound diffusion in highly scattering media.

An early technique for boundary removal in diffuse media was described in Ripoll et al. (2006) "From finite to infinite volumes: removal of boundaries in diffuse wave imaging." Phys. Rev. Lett. 96: 173903; the International (PCT) Patent Application Publication No. WO2007/072085, entitled, "Removal of Boundaries in Diffuse Media," and Greek Patent No. 1005346 (Application No. 20050100621), each of which are incorporated herein by reference. This technique is not suitable for use with fluorescence molecular tomography (FMT) or any other technique where quantitation is pursued. Where quantitation is pursued, as in the FMT approach, fluorescence must be considered in the context of the excitation source (referred to as the primary source), in which case fluorescence becomes a primary source-dependent secondary source. This means that the boundary removal equations used in the early technique are not sufficient to recover quantitatively the concentration of fluorophores, and would be adversely affected by tissue heterogeneity in general. In order to overcome these significant drawbacks, the virtual matching techniques of the present invention include transformation and use of the excitation source measurements to normalize the fluorescence measurements. This enables quantitative fluorescence imaging in heterogeneous media.

Preferred embodiments of the invention utilize a transformation that converts fluorescent data obtained from a diffusive object surrounded by free space (air, for example) into data that would be obtained if the same object were surrounded by an optically matching diffusive medium. This is done by applying the surface integral equations to an arbitrarily-shaped medium surrounded by free space and adding a term that would be present if the subject were embedded in a diffusive medium with the same optical properties. This "virtual index-matching" technique accounts for a refractive index mismatch between the media within the subject and the media (e.g., air) outside the subject. Once the data has been virtually index-matched it can be propagated within the virtual matched medium to a set of virtual detectors located arbitrarily and conforming to arbitrary geometries, including but not limited to, a planar array.

For example, in preferred embodiments, the detector data is transformed to its virtually-matched equivalent. This enables the use of infinite homogeneous functions for the weight matrix. This additionally enables full body imaging and the imaging of larger anatomies, since the complexity of reconstructing arbitrary shapes is now drastically reduced.

The invention provides systems and methods for transforming datasets to their virtually-matched equivalents for the purpose of reconstructing three-dimensional quantitative distributions of signal. These methods yield a faster and still accurate depiction of the localization and distribution of the signal in the object/subject, including quantification and distribution of signals, reporters and/or agents (i.e., contrast agents or probes) in such objects/subjects than can be achieved by conventional tomographic reconstruction techniques.

In accordance with certain embodiments of the present invention, fast tomographic reconstruction methods and algorithms can be applied by conforming the virtually-matched detectors to a planar array as described herein. The methods and algorithms have been fully parameterized to accommodate different imaging settings optimized for a variety of target objects/subjects and regions and a variety of different agents or probes. In particular, it is an object of the invention to provide such algorithms and a calibration and image correction analysis methods for use in biological research, as well as in preclinical and/or clinical settings. In particular, the present invention provides corrected and calibrated imaging algorithms that can optionally be used with one or more imaging agent or probes for in vivo molecular imaging.

In one aspect, the invention provides for a fluorescent molecular tomography system comprising: an excitation source; an optical imaging apparatus configured to direct light from the excitation light source into a subject at a plurality of locations; a detector configured to detect at multiple locations light emanating from a region within the subject; and a processor configured to process data corresponding to the detected light emanating from the region of the subject to produce a tomographic representation of the region of the subject, wherein the processor is configured to execute instructions to: (a) establish a forward model of excitation light propagation from the region to the detector using the data corresponding to the detected fluorescent light, wherein one or more virtual-matching transformation(s) is/are applied to the data corresponding to the detected fluorescent light to account for a refractive index discontinuity at the surface of the subject, and the forward model is established as a weight matrix of elements using one or more infinite homogeneous functions such that light propagation is modeled as if there is no discontinuity in refractive index at the surface of the subject; and (b) invert the weight matrix to obtain the tomographic representation of the region of the subject. In certain embodiments, in the forward model, the excitation light source is represented in real space and the detected fluorescent light is represented in frequency space (e.g., thereby facilitating hybrid reconstruction), and the tomographic representation of the region of the subject is a representation in real space. Furthermore, in the forward model, virtual detectors can be established that conform to an imposed geometry different from the arrangement of the actual detectors (e.g., and the forward model simulates light propagation from the region of the subject). For example, the imposed geometry can be a planar array.

In certain embodiments, the detector is further configured to detect at multiple locations excitation light emanating from the subject, and wherein the processor is configured to execute instructions to establish the forward model using the data corresponding to the detected excitation light and the detected fluorescent light. Furthermore, in certain embodiments, in the forward model, one or more virtual-matching transformations is/are applied to the data corresponding to the detected excitation light. In addition, in certain embodiments, in the forward model, the excitation light source is represented in real space, the detected excitation light is represented in frequency space, the detected fluorescent light is represented in frequency space, and the tomographic representation of the region of the subject is a representation in real space.

In certain embodiments, an experimental measurement of surface flux distribution is used in the forward model.

In certain embodiments, the detected fluorescent light is emitted from a probe within the region of the subject, and the forward model in (a) models excitation light propagation from the excitation light source to the probe and emitted fluorescent light propagation from the probe to the detector. In addition, in the forward model, a Born approximation is used to express an intensity of the detected fluorescent light emitted from the probe having spatially-varying concentration within the region. In other embodiments, the intensity of the detected fluorescent light is normalized using an intensity of the spatially-corresponding detected excitation light. In preferred embodiments, this facilitates the display of a quantitative concentration of a fluorophore within the subject by the tomographic representation of the region. The detected excitation light is preferably detected after passing through at least a portion of the subject, and the subject is preferably transilluminated with excitation light. In addition, the forward model is preferably established as a weight matrix of normalized elements. Furthermore, the forward model in (a) represents the detected excitation light and the detected fluorescent light in corresponding virtually-matched expressions.

In certain embodiments, the excitation light source or the optical imaging apparatus comprises a scanner configured to direct light into the subject at a plurality of locations, thereby defining a plurality of source locations. In certain embodiments, the plurality of source locations are non-uniformly spaced. In certain embodiments, the detector comprises an array of detector locations, and the forward model is established using data obtained from the array of detector locations. In certain embodiments, there are substantially more detector locations than source locations.

In certain embodiments, the optical imaging apparatus comprises a chamber. In other embodiments, the chamber is an animal chamber.

In certain embodiments, the subject is a human.

In certain embodiments, the excitation light is near-infrared light. In addition, the excitation light has a wavelength within a range from about 500 nanometers to about 1000 nanometers. In other embodiments, the excitation light has a wavelength within a range from about 635 nanometers to about 850 nanometers.

In certain embodiments, the excitation light is continuous wave (CW) light. The excitation light comprises at least one member selected from the group consisting of continuous wave light, time-resolved light, and intensity modulated light.

In certain embodiments, the forward model models excitation light propagation from the excitation light source to the region of the subject and fluorescent light propagation from the region to the detector, where there is free space between the surface of the subject and the detector.

In another aspect, the present invention provides methods for imaging using the virtual-matching transformation on the measured data in order to image the distribution of a fluorescent probe within a region of a subject, the method comprising the steps: (a) administering to the subject a probe comprising a visible or near-infrared fluorophore; (b) directing visible or near-infrared excitation light into the subject at multiple locations to transilluminate through or reflect from at least a portion of the region of the subject containing the fluorescent probe; (c) detecting excitation light transmitted through or reflected from the region of the subject; (d) detecting fluorescent light emitted from the probe within the subject; and (e) processing data corresponding to the detected fluorescent light, and, the detected excitation light, to provide a tomographic representation of the region of the subject, wherein the processing step comprises (i) establishing a forward model of excitation light propagation from an excitation light source to the probe within the subject and of emission light propagation from the probe to a detector using the data corresponding to the detected fluorescent light and, the detected excitation light, wherein: one or more virtual-matching transformation(s) is/are applied to the data corresponding to the detected fluorescent light and the data corresponding to the detected excitation light account for a refractive index discontinuity (e.g., mismatch) at the surface of the subject; an intensity of the detected fluorescent light is normalized using an intensity of spatially-corresponding detected excitation light; and the forward model is established as a weight matrix of normalized elements using one or more infinite homogeneous functions such that light propagation is modeled as if there is no discontinuity in refractive index at the surface of the subject; and (ii) inverting the weight matrix to obtain the tomographic representation of the region of the subject. In certain embodiments, in the forward model, the excitation light source is represented in real space and the detected fluorescent light is represented in frequency space (e.g., thereby facilitating hybrid reconstruction), and wherein the tomographic representation of the region of the subject is a representation in real space. Furthermore, in the forward model, virtual detectors can be advantageously established to conform to an imposed geometry different from the arrangement of the actual detectors (e.g., and the forward model simulates light propagation from the region of the subject to the virtual detectors). For example, the imposed geometry can be a planar array. In certain embodiments, the invention is a method of obtaining an experimental measurement of surface flux distribution for the surface of the subject, wherein the experimental measurement of surface flux distribution is used in the forward model. Furthermore, in the forward model, a Born approximation can be used to express an intensity of the detected fluorescent light emitted from the probe having spatially-varying concentration within the subject.

In certain embodiments, the forward model in step (e) represents the detected fluorescent light and the detected excitation light in corresponding virtually-matched expressions.

In another aspect, the present invention provides methods for imaging using a virtual-matching transformation technique to image the distribution of a fluorescence within a region of a subject, including but not limited to endogenous fluorescence, bioluminescence or fluorescent proteins, the method comprising: (a) directing excitation light into the subject at multiple locations to transilluminate through or reflect from at least a portion of the region of the subject containing the fluorescence; (b) optionally detecting excitation light transmitted through or reflected from the region of the subject; (c) detecting fluorescent light emitted from within the subject; and (d) processing data corresponding to the detected fluorescent light and the optionally detected excitation light to provide a tomographic representation of the region of the subject, wherein the processing step comprises (i) establishing a forward model of excitation light propagation from an excitation light source to the light source within the subject and of emission light propagation from the light source of the subject to a detector using the data corresponding to the optionally detected excitation light and the detected fluorescent light, wherein one or more virtual-matching transformation(s) is/are applied to the data corresponding to the detected fluorescent light and the data corresponding to the detected excitation light account for a refractive index discontinuity (e.g., mismatch) at the surface of the subject; optionally, an intensity of the detected fluorescent light is normalized using an intensity of spatially-corresponding detected excitation light; and the forward model is established as a weight matrix of normalized elements using one or more infinite homogeneous functions such that light propagation is modeled as if there is no discontinuity in refractive index at the surface of the subject; and (ii) inverting the weight matrix to obtain the tomographic representation of the region of the subject.

In certain embodiments, the method obtains one or more tomographic images which include a concentration map of the agent or probe in the heterogeneous diffuse object. In certain embodiments, the concentrations for the concentration map are determined using calibration measurements of a phantom (physical mock-up) of the heterogeneous diffuse object.

In addition, the tomographic representation can indicate an area of disease within a region of the subject. Furthermore, the tomographic representation can indicate an area of inflammation, arthritis, cancer, metastasis, plaque, infectious disease, cardiovascular disease, respiratory disease, metabolic disease, central nervous system disease, immune disease, neurodegenerative disease, dermatological disease, ophthalmic disease, cutaneous disease or a combination of two or more of the foregoing, within the region of the subject. In certain embodiments, the tomographic representation indicates a boundary of a disease site, such as a tumor within the region of the subject.

In certain embodiments, the probe used for imaging is an endogenous probe. In other embodiments, the probe may be exogenous and administered to the subject.

In certain embodiments, the probe comprises a member selected from the group consisting of a molecular probe, a fluorescent molecular probe, a phototherapy based fluorescent probe, an activatable fluorescent probe, an enzyme-activatable fluorescent probe, an activity based probe, a targeted fluorescent probe, a near-infrared fluorescent molecular probe, a fluorescent protein, a fluorescent biomolecule, a non-specific fluorescent probe, quantum dots, a receptor-targeted near-infrared fluorochrome, an antibody- or antibody-like targeted near-infrared fluorochrome, a wavelength-shifting beacon, a multi-color fluorescence probe, and a lanthanide metal-ligand probe. In addition, the probe may comprise a fluorochrome attached to a delivery vehicle comprising any one or more of a polymer, a dendrimer, a protein, a carbohydrate, a lipid sphere, and a nanoparticle.

In certain embodiments, the method of imaging comprises administering to the subject a plurality of probes having optically distinguishable fluorescent emission wavelengths, detecting fluorescent light emitted from each of the probes, and processing data corresponding to the detected light to provide one or more tomographic representations. In addition, the effect of the probe on the region within the object may be determined using the tomographic representation. Furthermore, the method may comprise imaging at excitation and emission wavelengths of a natural tissue chromophore.

In certain embodiments, imaging steps (b), (c), (d), and (e) may be repeated to obtain tomographic representations as a function of time. In addition, the kinetics of a distribution of the probe within the region can be monitored using tomographic representations. The kinetics of activation of the probe can be monitored using tomographic representations.

In certain embodiments, the method may comprise imaging at excitation and emission wavelengths of a natural tissue chromophore.

In certain embodiments, the tomographic representation comprises a map showing quantity of the probe in three dimensions. The tomographic representation may comprise one or more images, and the method may further comprise storing the one or more images, displaying the one or more images, or both storing and displaying the one or more images. In addition, the tomographic representation can include storing the one or more virtually-matched images, displaying the one or more virtually-matched images, or both story and displaying the one or more virtually-matched images. In addition, the tomographic representation may comprise a three-dimensional tomographic image, and the method may further comprise the step of combining the three-dimensional tomographic image with photographic, pictorial, magnetic resonance, x-ray computed tomography, ultrasound, single photon emission tomography, or positron-emission tomography imaging data and representations.

In certain embodiments, the imaging method further comprises the step of detecting or monitoring a cellular abnormality or disease using tomographic representation. The cellular abnormality or disease may comprise at least one member selected from the group consisting of cancer, oncological disease, infectious disease, metabolic disease, respiratory disease, cardiovascular disease, AIDS, immune disease, central nervous system disease, neurodegenerative disease, inflammation, dermatological disease, ophthalmic disease, cutaneous disease, inherited diseases, environmental diseases, bone-related diseases, immunologic disease, and surgery-related complications.

In certain embodiments, the subject of the imaging method is a mammal. In certain embodiments, the subject is a human.

In certain embodiments, the probe of the imaging method may comprise an endogenous fluorophore that is encoded by a gene within the subject. The expression of the gene encoding the fluorophore can be determined using tomographic representation. The endogenous fluorophore can be a fluorescent protein or biomolecule, including but not limited to green, red and infrared fluorescent proteins.

In each of the foregoing, the subject can be a mammal, for example, a human.

In another aspect, the invention is an apparatus for reconstructing a tomographic representation of a probe within a region of the subject, the apparatus comprising: a memory that stores code defining a set of instructions; and a processor that executes the instructions thereby to: (a) establish a forward model of excitation light propagation from an excitation light source to the probe within the region of the subject and of emission light propagation from the probe to a detector using data corresponding to detected fluorescent light from the probe and using data corresponding to detected excitation light transmitted through or reflected from the region of the subject, wherein one or more virtual-matching transformation(s) is/are applied to the data corresponding to the detected fluorescent light and the data corresponding to the detected excitation light to account for a refractive index discontinuity (e.g., mismatch) at the surface of the subject; an intensity of the detected fluorescent light is normalized using an intensity of spatially-corresponding detected excitation light; and the forward model is established as a weight matrix of normalized elements using one or more infinite homogeneous functions such that light propagation is modeled as if there is no discontinuity in refractive index at the surface of the subject; and (b) invert the weight matrix to obtain the tomographic representation of the region of the subject ace.

In certain embodiments, the processor executes the instructions to establish the forward model wherein the excitation light source is represented in real space, the detected fluorescent light and the detected excitation light are represented in frequency space, and the tomographic representation of the region of the subject is a representation in real space.

In another aspect, the invention can also provide for a diffuse optical tomography system comprising one or more illumination sources; an optical imaging apparatus configured to direct light from the at least one illumination source into a subject at a plurality of locations; a detector configured to detect at multiple locations light emanating from the subject to obtain a first and second measurement, wherein the first measurement is a reference measurement and the second measurement corresponds to absorption of at least a portion of the illuminating light as it passes through a light-absorbing region within the subject, and wherein the reference measurement does not reflect all of said absorption; and a processor configured to process data corresponding to the first and second measurements of detected light emanating from the subject, wherein the processor is configured to execute instructions to: (a) establish a forward model of light propagation from at least one of the one or more illumination sources to the light-absorbing region within the subject and of light propagation from the region to the detector using the data corresponding to the first and second measurements, wherein one or more virtual-matching transformation(s) is/are applied to the data corresponding to the detected fluorescent light to account for a refractive index discontinuity at the surface of the subject, and the forward model is established as a weight matrix of elements using one or more infinite homogeneous functions such that light propagation is modeled as if there is no discontinuity in refractive index at the surface of the subject; and (b) invert the weight matrix to obtain the tomographic representation of the region of the subject. In addition, the system can comprise at least two illumination sources having different wavelengths. In certain embodiments, the at least two illumination sources are near-infrared light sources.

In certain embodiments, a diffuse optical tomography imaging system can comprise at least two illumination sources with different wavelengths comprising a wavelength below an isosbestic point of an oxy-hemoglobin (HbO) and a deoxy-hemoglobin (Hb), and a wavelength above the isosbestic point.

In certain embodiments, step (b) of the method includes determining a concentration (or a concentration map) of the probe in the object using calibration measurements of a phantom (physical mock-up) of the object.

Elements from embodiments of one aspect of the invention may be used in other aspects of the invention (e.g., elements of claims depending from one independent claim may be used to further specify embodiments of other independent claims). Other features and advantages of the invention will be apparent from the following figures, detailed description, and the claims.

The objects and features of the invention can be better understood with reference to the drawings described below, and the claims. In the drawings, like numerals are used to indicate like parts throughout the various views.

DETAILED DESCRIPTION

Figure 1:
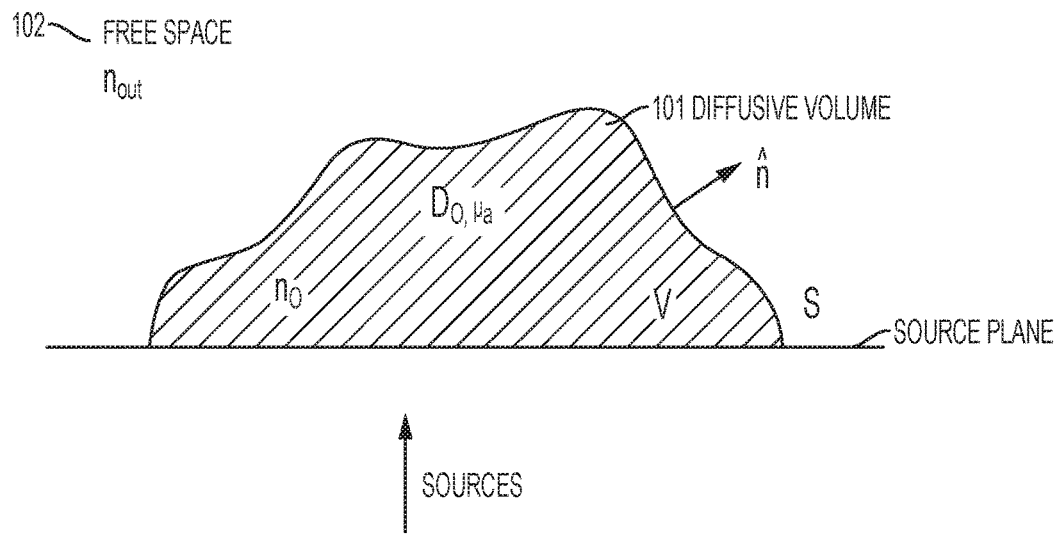
FIG. 1 is a schematic drawing depicting a diffusive volume V surrounded by free space, according to an illustrative embodiment of the invention.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

As used herein, the term "image" is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout).

The term "tomographic image" may refer, for example, to an optical tomographic image, an x-ray tomographic image, a tomographic image generated by magnetic resonance, positron emission tomography (PET), magnetic resonance, (MR) single photon emission computed tomography (SPECT), and/or ultrasound, and any combination of these.

The term "excitation image" is understood to mean an image acquired at the wavelength corresponding to that of the exposing light source, of said exposing light emanating from the object being imaged.

The terms "fluorescence image" or "emission image" are understood to mean an image acquired at the wavelength corresponding to the emission wavelength of a fluorescent agent or probe.

The term "residual image" is understood to mean the image resulting from the mathematical operation of subtracting a corrective term, for example an image, from an original image, for example a fluorescence image.

As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume, and the three-dimensional map may be displayed in two-dimensions.

As used herein, the term "electromagnetic radiation" is understood to mean self-propagating waves in space of electric and magnetic components that oscillate at right angles to each other and to the direction of propagation, and are in phase with each other. Electromagnetic radiation includes: radio waves, microwaves, red, infrared, and near-infrared light, visible light, ultraviolet light, X-rays and gamma rays.

As used herein, the term "image acquisition device" includes any detector of electromagnetic radiation including, but not limited to, CCD camera, photomultiplier tubes, photodiodes, and avalanche photodiodes.

As used herein, the term "virtually-matched" or "virtual-matching" is understood to mean measurements transformed through a virtual-matching transformation.

As used herein the term "virtual-matching method" or "virtual-matching approach" refers to a methodology that transforms the measurements taken at the surface of a subject surrounded by free space to the measurements that would exist if the subject were surrounded by a diffusive medium of optical properties equivalent to the average optical properties of the subject.

As used herein the term "virtually-matched medium" refers to a medium surrounding the subject with the same volume as that surrounding the subject that has the optical properties equal to the average optical properties of the subject.

As used herein the term "propagation of measurements" refers to the propagation of the virtually-matched measurements to a generic point in space outside of the subject, i.e. within the virtually-matched medium.

As used herein the term "virtual detectors" refers to the location in space outside of the subject, i.e. within the virtually-matched medium, of the detectors to which the virtually-matched measurements are propagated.

As used herein, the term "forward model" is understood to mean a physical model of light propagation in a given medium from a source to a detector.

A technique is described herein for tomographic reconstruction that performs a transformation on the detected intensities converting them into the virtually-matched expressions on subsets of tomographic datasets as described herein to enable the use of infinite homogeneous functions (i.e. functions that do not take into account the presence of the boundary) and to enable the propagation of these measurements to any point in the virtually-matched medium in order to perform fast tomographic reconstruction prior to image display and/or analysis. For the purposes of illustration, an illustrative, non-limiting description is provided for a method of fluorescence tomographic reconstruction in vivo of objects, e.g., reporters and/or agents such as contrast agents or probes, in a diffusive medium (e.g., a mammalian subject). This technique can be used in any of the tomographic systems described herein.

Fluorescence Molecular Tomography, abbreviated as FMT (sometimes also referred to as Fluorescence Mediated Tomography) or Diffuse Optical Tomography (when used to image concentration of absorbers), abbreviated as DOT, provide a method of in vivo imaging including the steps of administering to a subject an optical imaging probe; directing excitation light into the subject at multiple locations; optionally detecting excitation light emanating from the subject; detecting optical light emitted from one or more probes within the subject; and processing data corresponding to the detected fluorescent light emitted from the probe within the subject and, optionally, the detected excitation light emanating from the subject, to provide a tomographic representation of the region within the subject. The processing of data corresponding to both the detected excitation light and detected fluorescent light comprises simulating photon propagation at the excitation wavelength and simulating photon propagation at the emission wavelength to obtain a prediction of one or more quantitative measurements of the probe, such as concentration or total accumulation in a region within the object, and can also include additional steps of applying statistical optimal estimation and coincidence masking techniques to predict and compensate for waveguiding effects (see for example International Patent Application No. PCT/US2008/65648 "Imaging Systems Featuring Waveguiding Compensation"). The steps can also be repeated at predetermined intervals, thereby allowing for the evaluation of the subject over time. The subject may be a vertebrate animal, for example, a mammal, including a human. The subject may also be a non-vertebrate (for example, *C. elegans, drosophila*, or another model research organism, etc.) used in laboratory research.

In certain embodiments, the present invention can be used in FMT as well as DOT imaging systems. DOT is a technique that offers the capability to quantify changes in absorption present in highly scattering media such as tissue. Its theoretical principles are similar to FMT in the sense that sources need to be scanned on the object and light detected at a detector, assuming that light diffuses within the volume. In order for an absorption perturbation to be imaged in this modality a reference image where light has not been absorbed or that has been absorbed in a lesser manner needs to be taken. After this measurement, equivalent to the excitation measurement in FMT, a measurement where this absorption is present is acquired (equivalent to the emission measurement in FMT). By choosing appropriate wavelengths (e.g., in the near infrared), this technique may simultaneously quantify the tissue concentration of both oxy-(HbO) and deoxy-hemoglobin (Hb), and thus the oxygen saturation and blood volume. Typically, two or more near-infrared sources, chosen on both sides of the isosbestic point of the oxy/deoxyhemoglobin absorption spectrum (near 800 nm) are used to illuminate the tissue at various locations. The light intensity distribution at the tissue surface thus contains both spectral and spatial information about subsurface absorbers.

In certain embodiments, the invention can be used within a FMT imaging system comprising: an excitation light source; an optical imaging apparatus configured to direct light from the excitation light source into a subject at a plurality of locations; a detector configured to detect at multiple locations excitation light emanating from the subject and fluorescent light emanating from a region within the subject; and a processor configured to process data corresponding to the detected excitation light emanating from the subject and data corresponding to the detected fluorescent light emanating from the region of the subject to produce a tomographic representation of the region of the subject. The processor is configured to execute instructions to establish a forward model of excitation light propagation from the excitation light source to the region of the subject and of fluorescent light propagation from the region to the detector using the data corresponding to the detected excitation light and the detected fluorescent light. The excitation light source and the detected fluorescent light are transformed into their virtual-matched expression. Optionally, the virtually-matched measurements can then be propagated to an array of virtual detectors. Finally, the forward model is established as a discretized weight matrix of normalized elements which do not need to account for the presence of the surface; and the weight matrix is inverted to obtain the tomographic representation of the region of the subject in real space.

In the forward model, a surface of the subject is identified and boundary conditions are established for the surface. The boundary measurements are then transformed to the virtually-matched expressions corresponding to the surface of the subject in a virtually-matched infinite homogeneous medium, thereby simplifying the forward model. The data corresponding to the surface of the subject surrounded by free space comprises an experimental measurement of surface flux distribution. The forward model then models excitation light propagation from the excitation light source to the region of the subject and fluorescent light propagation from the region to the detector, where now there is no free space between the surface of the subject and the detector and the medium has been replaced by a virtually-matched medium with the optical properties equal to the average optical properties of the subject.

In certain embodiments, the detected fluorescent light is emitted from a probe within the region of the subject, and the forward model then models excitation light propagation from the excitation light source to the probe and emitted fluorescent light propagation from the probe to the detector. In the forward model, a Born approximation is used to express an intensity of the detected fluorescent light emitted from the probe having spatially-varying concentration within the region. The intensity of the detected fluorescent light is normalized using an intensity of the spatially-corresponding detected excitation light.

In other embodiments, the forward model represents the detected excitation light and the detected fluorescent light transformed into their virtually-matched expressions. In the system, the excitation light source or the optical imaging apparatus comprises a scanner configured to direct light into the subject at a plurality of locations, thereby defining a plurality of source locations. With the virtually-matched expressions, a non-uniform grid of any number of sources can be used. The detector comprises an array of detector locations which can be arbitrary or be conformed to a simple geometry such as a plane, and the forward model is established using data obtained from a plurality of detector locations.

In certain embodiments of the system, the excitation light is near-infrared. The excitation light has wavelength within a range from about 500 nanometers to about 1000 nanometers. In other embodiments of the system, the excitation light has wavelength within a range from about 635 nanometers to about 850 nanometers. Furthermore, the excitation light is continuous wave (CW) light. The excitation light comprises at least one member selected from the group consisting of continuous wave light, time-resolved light, and intensity modulated light.

The method and algorithm accept as input raw scan images generated by a fluorescence molecular tomography (FMT) system acquisition of any object. As described in U.S. Pat. No. 6,615,063 "Fluorescence-Mediated Molecular Tomography", U.S. patent application Ser. No. 11/003,936 "Imaging Volumes with Arbitrary Geometries in Contact and Non-Contact Tomography", and International Patent Application No. PCT/US2004/003229 "Method and System for Free Space Optical Tomography of Diffuse Media", the texts of which are incorporated herein by reference in their entirety, FMT-generated raw scan images contain images at both the excitation wavelength of the light source, called "excitation images", and at the emission wavelength of the contrast agent, interchangeably called "emission images" or "fluorescence images", for a multiplicity of source and/or detector locations. The raw scan images can be optionally pre-processed to detect and compensate for the effects of optical heterogeneity in the medium, as described in International Patent Application No. PCT/US2008/65648 "Imaging Systems Featuring Waveguiding Compensation".

In preferred embodiments, the detected light preferably includes excitation light from the light source that has been transmitted through or reflected from the object and fluorescent light emitted from one or more fluorophore within the object. In the case of DOT, only the excitation light from the light source that has been transmitted through the object is detected. Data corresponding to the excitation light transmitted through or reflected from the object can be used to correct/calibrate captured fluorescent measurements, thereby providing more accurate tomographic images. The one or more fluorophore emits fluorescent light as a result of excitation by the excitation light. Background fluorescence may be accounted for by obtaining background measurements and processing data corresponding to the captured fluorescent light accordingly. For example, the method may include the step of detecting a background signal, where the processing step includes generating a corrected measurement of the detected fluorescent light and/or a corrected measurement of the detected excitation light using data corresponding to the detected background signal, and using the corrected measurement(s) in the optical tomographic reconstruction. In certain embodiments, the processing step includes generating a corrected measurement of the detected fluorescent light and a corrected measurement of the detected excitation light using data corresponding to the detected background light, generating a calibrated fluorescent measurement from the corrected fluorescent measurement and the corrected excitation light measurement, and using the calibrated fluorescent measurement in the optical tomographic reconstruction.

Data corresponding to the detected light may be used as input in the optical tomographic and/or planar reconstruction, for example, in an iterative process. In certain embodiments, the steps of the method are repeated to obtain a plurality of tomographic and/or planar images. In certain embodiments, the steps of the method are repeated to obtain tomographic representations as a function of time. In other embodiments, the kinetics of distribution of a probe within a region are monitored using tomographic representations. In another aspect, the kinetics of activation of a probe within a region are monitored using tomographic representations.

In other embodiments, the invention is a method of imaging a distribution of a fluorescent probe within a region of a subject, the method comprising: (a) administering to the subject a probe comprising a visible or near-infrared fluorophore; (b) directing visible or near-infrared excitation light into the subject at multiple locations to reflect from or transilluminate at least a portion of the region of the subject containing the fluorescent probe; (c) optionally detecting excitation light transmitted through or reflected from the region of the subject; (d) detecting fluorescent light emitted from the probe within the subject; and (e) processing data corresponding to the detected fluorescent light and the optionally detected excitation light to provide a tomographic representation of the region of the subject, wherein the processing step comprises: (i) establishing a forward model of excitation light propagation from an excitation light source to the light source within the subject and of emission light propagation from the light source of the subject to a detector using the data corresponding to the optionally detected excitation light and the detected fluorescent light, wherein: (A) a surface of the subject is identified and boundary conditions are established for the surface; (B) The surface measurements are transformed into their virtually-matched expressions which simulate an infinite homogeneous medium, thereby simplifying the forward problem; (C) the virtually-matched fluorescent light and, optionally, the virtually-matched excitation light, are propagated to a planar, or optionally, an arbitrary, configuration of virtual detectors, which would enable the use of fast inversion algorithms; and (D) the forward model is established as a discretized weight matrix of normalized elements which do not need to account for the boundary; and (ii) inverting the weight matrix to obtain the tomographic representation of the region of the subject in real space.

In certain embodiments, the tomographic representation comprises a map of concentration of the probe within the region of the subject. In other embodiments, the tomographic representation comprises a map showing quantity of the probe in three dimensions. In addition, the tomographic representation comprises one or more images, and wherein the method further comprises storing the one or more images, displaying the one or more images, or both storing and displaying the one or more images. In other embodiments, the tomographic representation comprises a three-dimensional tomographic image and wherein the method further comprises the step of combining the three-dimensional tomographic image with magnetic resonance, x-ray computed tomography, ultrasound, single photon emission tomography, or positron emission tomography imaging data.

In certain embodiments, the probe used for imaging is an endogenous probe. Furthermore, the probe may comprise an endogenous fluorophore that is encoded by a gene within the subject. In other embodiments, the invention is a method for determining expression of the gene encoding the fluorophore using the tomographic representation. In other embodiments, the endogenous fluorophore is a fluorescent protein or biomolecule. In other embodiments, the invention is a method comprising the step of imaging at excitation and emission wavelengths of a natural tissue chromophore.

In other embodiments, the probe used for imaging is administered to the subject. In certain embodiments, the invention includes methods for imaging with probes wherein step (a) comprises administering to the subject a plurality of probes having optically distinguishable fluorescent emission wavelengths, step (d) comprises detecting fluorescent light emitted from each of the probes, and step (e) comprises processing data corresponding to the detected light to provide one or more tomographic representations. In other embodiments, the invention is used to determine an effect of the probe on the region within the object using the tomographic representation. The probe comprises a member selected from the group consisting of a molecular probe, a fluorescent molecular probe, an activatable fluorescent probe, an enzyme-activatable fluorescent probe, a targeted fluorescent probe, a near-infrared fluorescent molecular probe, a fluorescent protein, a fluorescent biomolecule, a non-specific fluorescent probe, quantum dots, a receptor-targeted near-infrared fluorochrome, an antibody-targeted near-infrared fluorochrome, a wavelength-shifting beacon, a multi-color fluorescence probe, and a lanthanide metal-ligand probe. In other embodiments, the probe comprises a fluorochrome attached to a delivery vehicle comprising any one or more of a polymer, a dendrimer, a protein, a carbohydrate, a lipid sphere, and a nanoparticle.

In another aspect, the invention relates to a method of imaging a target volume of an object, the method including the steps of directing excitation radiation into the object at multiple locations; optionally detecting excitation radiation transmitted through or reflected from the object; detecting radiation at a surface of the object; detecting radiation emitted from one or more contrast agents/probes within the object; and processing data corresponding to the detected radiation transmitted through or reflected from the object, the optionally detected excitation radiation transmitted through or reflected from the object, and the detected radiation emitted from the one or more contrast agents/probes within the object to provide one or more images of the target volume of the object. The method may further include the step of displaying the image. The object may be, for example, an animal, for example, a mammal, or a human.

In another aspect, the invention relates to a method for detecting disease. In certain embodiments, the tomographic representation indicates an area of disease within the region of the subject. In other embodiments, the tomographic representation indicates an area of arthritis, cancer, metastasis, plaque, or a combination of two or more of the foregoing, within the region of the subject. In other embodiments, the tomographic representation indicates a boundary of a tumor within the region of the subject. In other embodiments, the tomographic representation can be used to detect or monitor a cellular abnormality or disease. Furthermore, the cellular abnormality or disease comprises at least one member selected from the group consisting of cardiovascular disease, AIDS, neurodegenerative disease, inflammation, dermatological disease, ophthalmic disease, cutaneous disease, and immunologic disease.

Algorithms that support preferred embodiments of the invention are detailed below. FIG. 1 is a schematic drawing depicting a diffusive volume V 101 surrounded by Free space, i.e. an otherwise infinite homogeneous and non-diffusive medium 102. The geometry shown in FIG. 1, consists of a diffusive volume V 101 bounded by surface S, which separates it from an outer non-diffusive medium 102 of refractive index $n_{out}$. The diffusive medium is characterized by its absorption coefficient $\mu_a$, its reduced scattering coefficient $\mu_s'$ (defined as $\mu_s'=\mu_s(1-g)$, where g is the anisotropy factor), and its average refractive index $n_{in}$. In a highly absorbing and scattering medium the diffusion coefficient may be defined as $D=\frac{1}{3}(\mu_s'+\alpha\mu_a)$, the factor $\alpha$ depending non-linearly on the optical properties and having typically values between $\alpha=0.2$ to $\alpha=0.6$ (see Ripoll, J., D. Yessayan, et al. (2004). "Experimental determination of photon propagation in highly absorbing and scattering media." J. Opt. Soc. Am. A 22(3) and references therein for a deeper study of this factor and experimental validation). Typical values of $\alpha$ for tissue in the visible (where tissue absorption is greater) are in the order of $\alpha=0.5$ for typical values of anisotropy in tissue of $g\sim0.8$. In preferred embodiments, the invention deals directly with D and $\mu_a$, instead of $\mu_s'$ and $\mu_a$, assuming they are related through the above mentioned expression. Additionally, all derivation is done in the frequency domain, with the extrapolation to time-domain through a Fourier transform, or to the CW regime by straightforward selection of the zero frequency component.

Assume that in the volume V 101 of FIG. 1, a point source located at $r_s$ inside the medium whose intensity is modulated at a frequency $\omega$. In this case, the average intensity U may be expressed as $U(r,t)=U(r)\exp[-i\omega t]$. Accounting for energy conservation in the Radiative Transfer Equation, the U detected at r within V represents a diffuse photon density wave (DPDW) and obeys the Helmholtz equation:

$$\nabla^2 U(r) + \kappa_0^2 U(r) = -\frac{S(r)}{D} \quad r \in V, \tag{1}$$

with a complex wave-number $\kappa_0$ given by:

$$\kappa_0 = \left(-\frac{\mu_a}{D} + i\frac{\omega n_{in}}{cD}\right)^{1/2} \tag{2}$$

where c is the speed of light in vacuum and S(r) is the source distribution. In an infinite homogeneous 3D medium the Green function accounting for light propagation from source to detector is given by:

$$g(\kappa_0 | r_s - r_d |) = \frac{\exp(i\kappa_0 | r_s - r_d |)}{D | r_s - r_d |} \tag{3}$$

Taking into account rigorously the boundary S, the average intensity $U^{srf}$ inside volume V which takes into account the presence of the boundary is found through Green's theorem as [J. Ripoll and M. Nieto-Vesperinas, J. Opt. Soc. Am. A 16, 1453 (1999)]:

$$U^{srf}(r_d) = U^{(inc)}(r_d) - \tag{4}$$

$$\frac{1}{4\pi}\int_S\left[U^{srf}(r')\frac{\partial g(\kappa | r' - r_d |)}{\partial \hat{n}'} - g(\kappa | r' - r_d |)\frac{\partial U^{srf}(r')}{\partial \hat{n}'}\right]dS',$$

where $$U^{(inc)}(r) = \int_V S(r)g(\kappa_0 | r_s - r_d |)d^3r \tag{5}$$

is the average intensity that is obtained in the absence of the surface. One can use Fick's Law:

$$J_n(r) = J(r)\cdot\hat{n} = -D\frac{\partial U^{srf}(r)}{\partial \hat{n}} \tag{6}$$

and the boundary condition between the diffusive and non-diffusive medium (R. Aronson, J. Opt. Soc. Am. A 12, 2532 (1995)):

$$U^{srf}(r)|_S = -C_{nd}D\frac{\partial U^{srf}(r)}{\partial \hat{n}}\bigg|_S, r \in S \tag{7}$$

$$U^{srf}(r)|_S = C_{nd}J_n(r)|_S, r \in S$$

where the coefficient $C_{nd}$ takes into account the refractive index mismatch between both media (R. Aronson, J. Opt. Soc. Am. A 12, 2532 (1995)). In the case of index matched media, i.e. $n_{out}=n_{in}$, $C_{nd}=2$, whereas for typical tissue/air index values (nin=1.333, nout=1) $C_{nd}\sim 5$. Making use of Eqs. (6) and (7) in Eq. (4), there is a convenient expression which depends solely on the total flux $J_n$ so that Eq. (4) can be rewritten as:

$$U^{srf}(r) = U^{(inc)}(r) + \tag{8}$$

$$\frac{1}{4\pi D}\int_S\left[C_{nd}D\frac{\partial g(\kappa | r' - r |)}{\partial n'} + g(\kappa | r' - r |)\right]J_n(r')dS', r \in V$$

In order to simplify further derivations, the surface integral $\Sigma^+(J_n)$ is defined as the surface contribution of the measured flux $J_n$ as follows:

$$\Sigma^+(J_n) = \frac{1}{4\pi D}\int_S\left[C_{nd}D\frac{\partial g(\kappa | r' - r |)}{\partial n'} + g(\kappa | r' - r |)\right]J_n(r')dS', r \in V \tag{9}$$

In terms of Eq. (8) we may write the average intensity at the boundary $U^{srf}$ which takes into account the interface and the general surface S as:

$$U^{srf}(r)=U^{(inc)}(r)+\Sigma^+(J_n) \tag{10}$$

Eq. (9) represents the average intensity accounting for the presence of the surface S.

Consider now the case where instead of having the volume V 101 surrounded by free space (see FIG. 5), the same volume is surrounded by a medium with the same optical properties as those of the diffusive object of volume V, i.e. D, $\mu_a$, and $n_{in}$. In this case, the average intensity would not reflect the presence of the boundary, since by having a medium surrounding volume V of the same properties, the optical discontinuity-generated boundary effect would disappear. The expression accounting for this is referred to in the present specification as the virtually-matched expression. This expression is determined from the surface-dependent expression in Eq. (10). In order to do this, note that the virtually-matched case shown in FIG. 5 can be reduced to the sum of the actual measurement FIG. 1 with its inverted situation, FIG. 4. That is, if the contribution of the missing volume is added to the surface-dependent expression Eq. (10), the average intensity that would be present in the absence of the surface is obtained. The contribution of the volume that surrounds the subject V that yields the virtually-matched average intensity is given by:

$$\Sigma^{-}(J_n) = -\frac{1}{4\pi D}\int_S \left[C_{nd}D\frac{\partial g(\kappa|r'-r|)}{\partial n'} + g(\kappa|r'-r|)\right]J_n(r')dS' + \Sigma^{(\infty)} \quad (11)$$

where $\Sigma^{(\infty)}$ represents the surface integral at a sphere of infinite radius, which as long as $\mu_a > 0$ becomes $\Sigma^{(\infty)} = 0$, since the Green function at infinity is zero. Note that the minus sign in Eq. (11) comes from the fact that now $J_n$ and the surface normal n point in opposite directions. Using Eq. (11), the virtual-matched solution $U^{VM}$, i.e. the average intensity that would be present in the absence of the interface would be given by:

$$U^{VM}(r) = U^{srf} + \Sigma^{-}(J_n) \quad (12)$$

Making use of the boundary conditions which relate the measured flux $J_n$ to the surface-dependent average intensity $U^{srf}$ Eq. (12) may be rewritten as:

$$U^{VM}(r) = C_{nd}J_n + \Sigma^{-}(J_n) \quad (13)$$

In order to demonstrate that this expression is equivalent to the average intensity that would exist in the absence of the interface, substitute Eq. (12) into Eq. (10) to obtain:

$$U^{VM}(r) = U^{srf}(r) + \Sigma^{-}(J_n) = U^{(inc)}(r) + \Sigma^{-}(J_n) + \Sigma^{+}(J_n)$$

$$U^{VM}(r) = U^{(inc)}(r) \quad (14)$$

since $\Sigma^{+}(J_n)$ and $\Sigma^{-}(J_n)$ cancel out. Rewriting explicitly Eq. (13), the virtual-matching transformation is expressed as:

$$U^{VM}(r) = C_{nd}J_n - \frac{1}{4\pi D}\int_S \left[C_{nd}D\frac{\partial g(\kappa|r'-r|)}{\partial n'} + g(\kappa|r'-r|)\right]J_n(r')dS' \quad (15)$$

It is important to note that in the virtual-matching expression shown in Eq. (15), $J_n$ are the actual measurements obtained from the detector, once the free-space propagation contribution has been taken into account. There is therefore no need to solve the integral Eq. (8) where one usually either solves for the surface flux $J_n$ or for the average intensity U at the boundary, as is typically achieved by using accurate algorithms such as the Diffuse Reflectance Boundary Method (Ripoll, J. and V. Ntziachristos (2003), "Iterative boundary method for diffuse optical tomography." J. Opt. Soc. Am. A 20(6): 1103-1110.) or approximations to it such as the Kirchhoff Approximation (Ripoll, J., V. Ntziachristos, et al. (2001), "The Kirchhoff Approximation for diffusive waves." Phys. Rev. E 64: 051917: 1-8.). Note that all the Green functions, g, involved in Eq. (8) are infinite Green's functions.

Considering that the measurements at our detector are given by $J_n^{meas}$, it is known that these are related to the flux at the surface $J_n$ as:

$$J_n^{meas}(r_d) = J_n(r)f_{air}(r - r_d), r \in S \quad (16)$$

where $f_{air}$ is a function which takes into account diffuse light propagation in free space, as shown in Ripoll and Ntziachristos (2006) "From finite to infinite volumes: removal of boundaries in diffuse wave imaging." Phys. Rev. Lett. 96(17): 173903 and International Patent Application No. PCT/US2004/003229 "Method and System for Free Space Optical Tomography of Diffuse Media". Note that $f_{air}$ becomes a convolution with $J_n$ in the more general case where out-of-focus measurements are included, which is not shown here, but is included in the present invention. Eq. (16) can be applied to Eq (15).

Having determined the virtual-matching transformation, Eq. (15), consider the special instance where we want the location of the detectors (currently on the surface S by using Eq. (16)) to be on a generic plane within the virtually-matched medium. To that end the first Rayleigh-Sommerfeld integral formula is used, which states that for a flat surface A at $z = z_o$ the field (in this case the average intensity) at $z > z_o$ is given by (Born and Wolf, Principles of Optics):

$$U(r) = \frac{1}{2\pi}\int_A U(r')\frac{\partial g(\kappa|r - r'|)}{\partial z'}dA', \forall z > z_o \quad (17)$$

where A in this case is in the (xy) plane in order for Eq. (17) to be valid. In general terms we may rewrite Eq. (17) for the virtually-matched expression $U^{VM}$ for a generic surface with surface normal n as:

$$U_{prop}^{VM}(r_d) = \frac{1}{2\pi}\int_S U^{VM}(r')\frac{\partial g(\kappa_0|r - r'|)}{\partial n'}dS' \quad (18)$$

where $U_{prop}^{VM}(r_d)$ now stands for the virtual-matched expression propagated to virtual detectors located at $r_d$. Note that Eq. (18) only holds for values outside of volume V. Additionally, this expression is exact for a plane surface, and represents an approximation in the more general case. The exact expression would be such that (see Eq. (4) for comparison):

$$U_{prop}^{VM}(r_d) = \frac{1}{2\pi}\int_S \left[U^{VM}(r')\frac{\partial g(\kappa_0|r - r'|)}{\partial n'} + \frac{1}{D}g(\kappa_0|r - r'|)J^{VM}(r')\right]dS' \quad (19)$$

where we have made use of Fick's law, Eq. (7). However, the quantity $J^{VM}$ is unknown, since we can only recover $U^{VM}$ from our measurements. In any case it should be noted that within the diffusion approximation $J^{VM} \ll U^{VM}$ as shown in Ishimaru, Ishimaru (1978), *Wave propagation and scattering in Random Media*, New York, Academic. Thus, Eq. (18) is a good approximation even in the presence of arbitrary interfaces.

Once the virtual-matching transformation Eq. (15) is defined and the expression that enables the propagation of these virtually-matched values to any point in space outside of volume V is determined using Eq. (19), these may be applied to the fluorescence and excitation measurements in order to solve the inverse problem.

Figure 6:
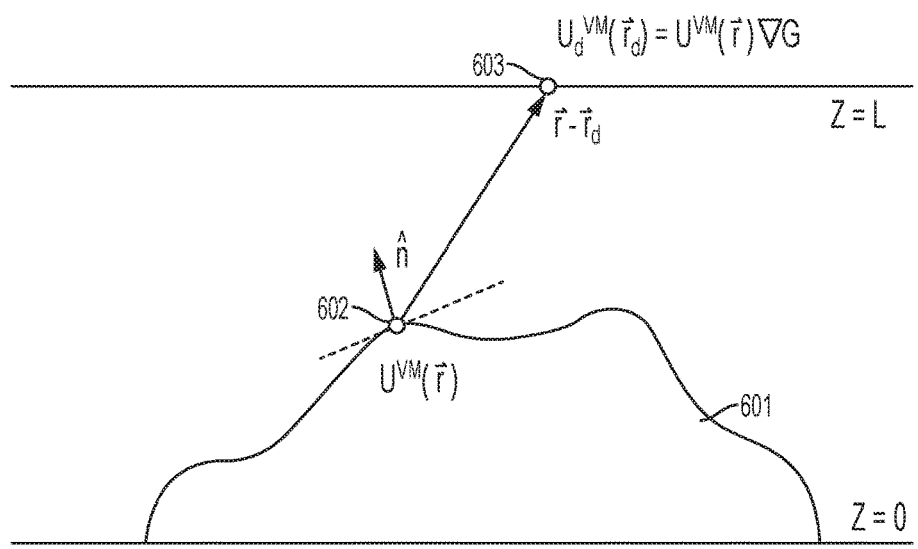
FIG. 6 is a schematic drawing depicting that once the data has been converted to the virtually-matched expression, it can be propagated through the virtual-matching diffusive medium from the surface position to an arbitrary virtual detector, according to an illustrative embodiment of the invention.

Assume that within volume V 601 of FIG. 6 there is a collection of fluorophores with spatially-dependant concentration F(r). The fluorescence intensity due to a collection of fluorophores with concentration F(r) distributed within a volume V in an otherwise infinite homogeneous medium may be expressed within the Born approximation as:

$$U_{fl}(r_s, r_d) = \int_V U^{srf}(r_s, r) F(r) G(r, r_d) dr \quad (20)$$

where G is the Green's function that takes into account the surface of volume V. Applying the virtual-matching transformation, we may rewrite Eq. (20) as:

$$U_{fl}^{VM}(r_s, r_d) = \int_V U^{srf}(r_s, r) F(r) g(r, r_d) dr \quad (21)$$

where now g represents the infinite homogeneous green's function given by Eq. (3) and $U_{fl}^{VM}(r_s, r_d)$ could include the propagation to virtual detectors or correspond to the value of the virtual-matched expression at the surface of the subject. The normalized Born expression (see for example Ntziachristos and Weissleder (2001) "Experimental three-dimensional fluorescence reconstruction of diffuse media using a normalized Born approximation." Opt. Lett. 26(12): 893-895) for the virtually-matched expressions will be therefore given by:

$$U_n^{VM} = \frac{U_{fl}^{VM}(r_s, r_d)}{U_{ex}^{VM}(r_s, r_d)} = \int_V \frac{U^{srf}(r_s, r) F(r) g(r, r_d) dr}{S_0(r_s) g(r_s, r)} \quad (22)$$

where we have written:

$$U_{ex}^{VM}(r_s, r_d) = U^{(inc)}(r_s, r_d) = S_0(r_s) g(r_s, r_d) \quad (23)$$

with $S_0$ being the excitation source strength. In Eq. (22) the average intensity inside volume V, $U^{srf}$ is given by Eq. (4):

$$U^{srf}(r_s, r) = U^{(inc)}(r_s, r) + \Sigma_V(U^{srf}) \quad (24)$$

where we have written $\Sigma_V(U^{srf})$ as:

$$\Sigma_V(U^{srf}) = U^{(inc)}(r) - \frac{1}{4\pi} \quad (25)$$

$$\int_S \left[ U^{srf}(r') \frac{\partial g(\kappa|r'-r_d|)}{\partial \hat{n}'} - g(\kappa|r'-r|) \frac{\partial U^{srf}(r')}{\partial \hat{n}'} \right] dS', r \in V$$

Introducing Eq. (25) into Eq. (22) we obtain the virtually-matched expression for the normalized Born approximation:

$$U_n^{VM} = \frac{U_{fl}^{VM}(r_s, r_d)}{U_{ex}^{VM}(r_s, r_d)} = $$

$$\int_V \frac{g(r_s, r) F(r) g(r, r_d)}{g(r_s, r)} dr + \int_V \Sigma_V(U^{srf}) \frac{F(r) g(r, r_d)}{S_0(r_s) g(r_s, r)} dr \quad (26)$$

Equation (26) is general and takes into account all possible contributions of the surface S. However, for practical applications the second term in Eq. (26) can be neglected since the contribution to the leading term is less than 10%, reaching a much more manageable expression for the normalized Born approximation for virtually-matched measurements:

$$U_n^{VM} = \frac{U_{fl}^{VM}(r_s, r_d)}{U_{ex}^{VM}(r_s, r_d)} \approx \int_V \frac{g(r_s, r) F(r) g(r, r_d)}{g(r_s, r)} dr \quad (27)$$

By following Eq. (27) it is now possible to make use of infinite homogeneous green's functions to solve our inverse problem:

$$U_n^{VM}(r_s, r_d) = \sum_{i=1}^{N} W(r_s; r_d; r_i) F(r_i) \quad (28)$$

where W is the weight matrix:

$$W(r_s; r_d; r_i) = \frac{1}{4\pi D} \left[ \frac{g(r_s, r_i) g(r_i, r_d) \Delta V}{g(r_s, r_d)} \right] \quad (29)$$

In order to obtain a 3D reconstruction of fluorescent agent concentration, or of absorber concentration, we need to solve for:

$$[F_m]_{1 \times M} = [W_{s,i}^m]_{M \times (N_s \times N_d)}^{-1} [U_n^{VM(s,i)}] \quad (25)$$

where m is the voxel index for a total of M voxels, s is the source index for a total of Ns external sources and i is the detector index for a total of Nd detectors.

There are several approaches that can be used to solve Eq. (25). Examples of approaches that could be used for solving for the concentration of fluorescent agent or absorbers, F are iterative approaches (such as the Algebraic Reconstruction Technique), Singular Value Approaches (Singular Value Decomposition, Tikhonoff Regularization, etc), Gradient Methods, etc. The weight matrix has a simplified expression due to the use of infinite homogeneous functions, enabling faster inversion.

Figure 2:
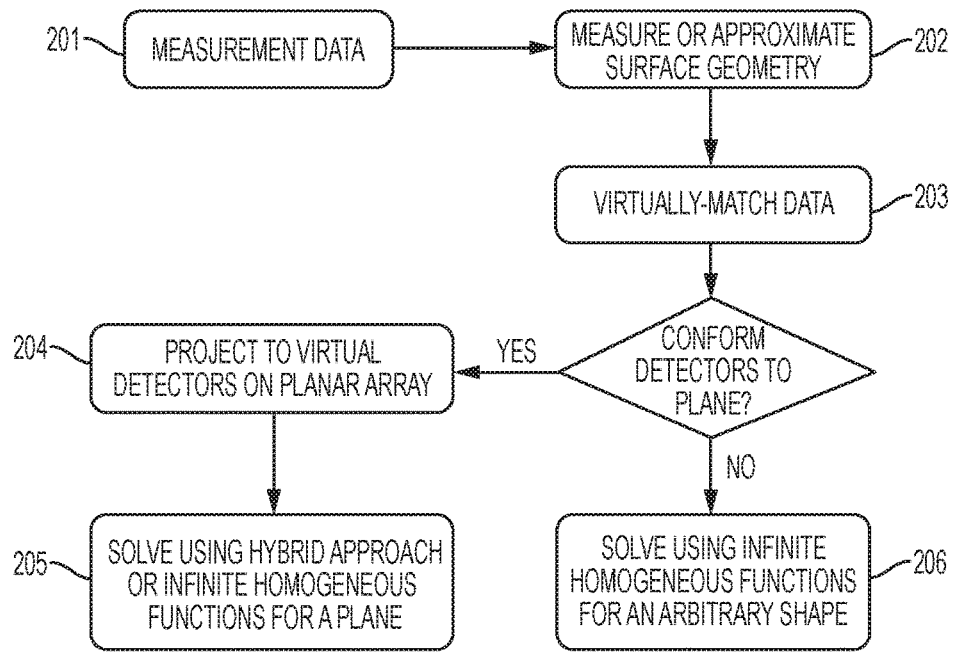
FIG. 2 is a block diagram of the steps of a method for obtaining a quantitative 3D distribution of a fluorescing or absorbing probe, tissue, or other target object in a subject, according to an illustrative embodiment of the invention.

FIG. 2 is a block diagram of the steps of a method for obtaining a quantitative 3D distribution of a fluorescing or absorbing probe, tissue, or other target object in a subject, according to an illustrative embodiment of the invention. This block diagram compares the steps used in preferred embodiments of this invention after virtual-matching transformation on the surface data 203 (e.g., conforming the detectors to a planar array 204 in order to use the Hybrid Inversion approach 205) with those used in a conventional imaging approach using infinite homogenous functions to invert the problem 206. First, measurement data 201 is obtained, then surface geometry is measured or approximated 202 and virtual matching 203 is performed as described herein above. Then, in preferred embodiments, detectors are conformed to a plane 204 such that either the Hybrid Inversion approach 205 can be used, or infinite homogeneous functions for a plane are used. Where detectors are not conformed to a plane, infinite homogeneous functions may be solved for an arbitrary shape 206, although computation time may be considerably higher.

Figure 3:
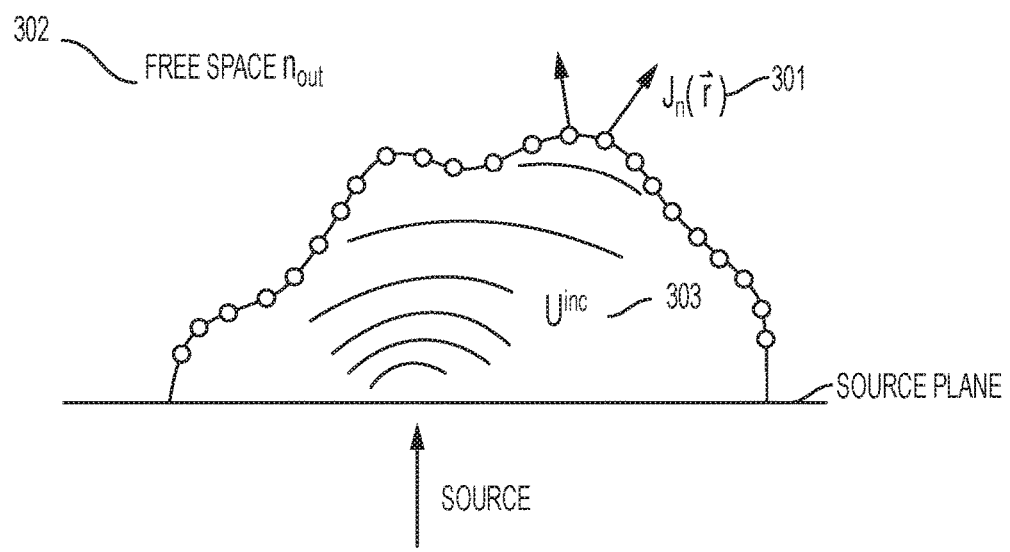
FIG. 3 is a schematic drawing depicting flux that leaves the subject at its surface, according to an illustrative embodiment of the invention.

FIG. 3 depicts the flux 301 that leaves the subject at its surface. The flux 301 is then measured by the detector after it travels through Free space 302. The flux 301 at the boundary is produced by an average intensity 303 propagating inside the subject that was generated by a source or collection of sources or fluorophores.

Figure 4:
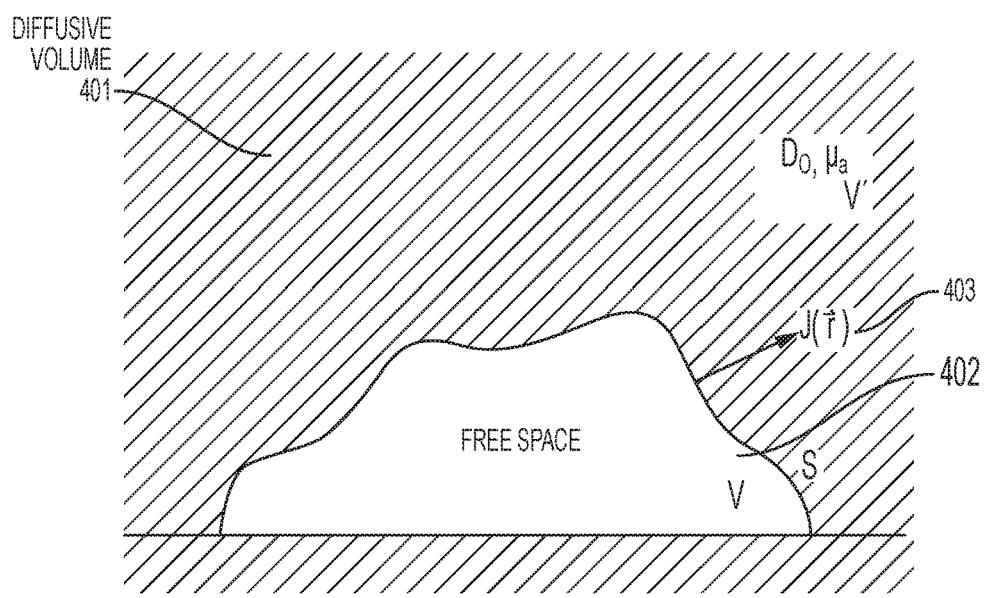
FIG. 4 is a schematic drawing depicting the inverted situation where the subject is embedded in an otherwise infinite and homogeneous diffusive medium of identical optical properties to those of the subject, according to an illustrative embodiment of the invention.

FIG. 4 depicts the inverted situation from FIG. 2, where now the subject is embedded in an otherwise infinite and homogeneous diffusive medium 401 of identical optical properties to those of the subject where now the volume occupied by the subject is non-scattering, i.e. Free space 402, and now we have a flux propagating into the diffusive medium 403.

Figure 5:
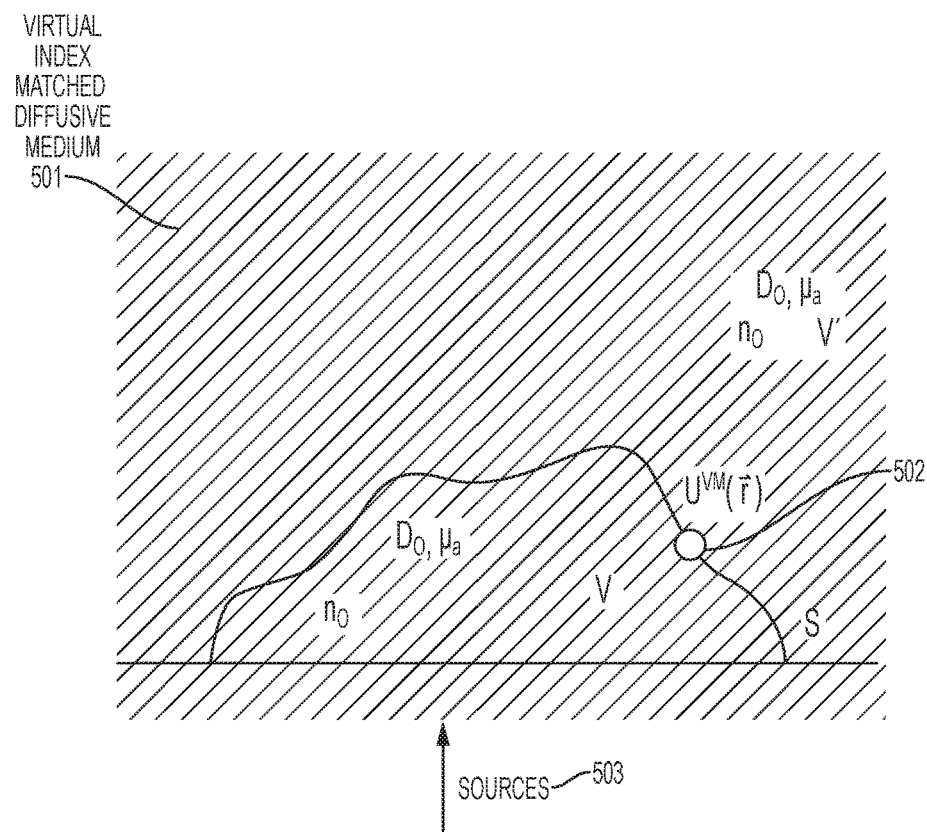
FIG. 5 is a schematic drawing depicting the effect of virtually-matching the measurements to a medium with the same average optical properties of the subject, according to an illustrative embodiment of the invention.

FIG. 5 is a schematic showing the effect of virtually-matching the measurements 502, to a medium with the same average optical properties of the subject 501, with the sources 503 in the same original position. The solution to this problem is equivalent to solving for the source positions 503 in the absence of a boundary.

FIG. 6 is a graph illustrating how once the data has been converted to the virtually-matched expression 601 it can be propagated through the virtual-matching diffusive medium from the surface position 602 to an arbitrary virtual detector 603. By projecting all values from a complex surface to a simple geometry such as a plane, other fast inversion approaches such as the Hybrid Inversion approach can be used to recover the 3D distribution of the fluorophores, for example.

Figure 7:
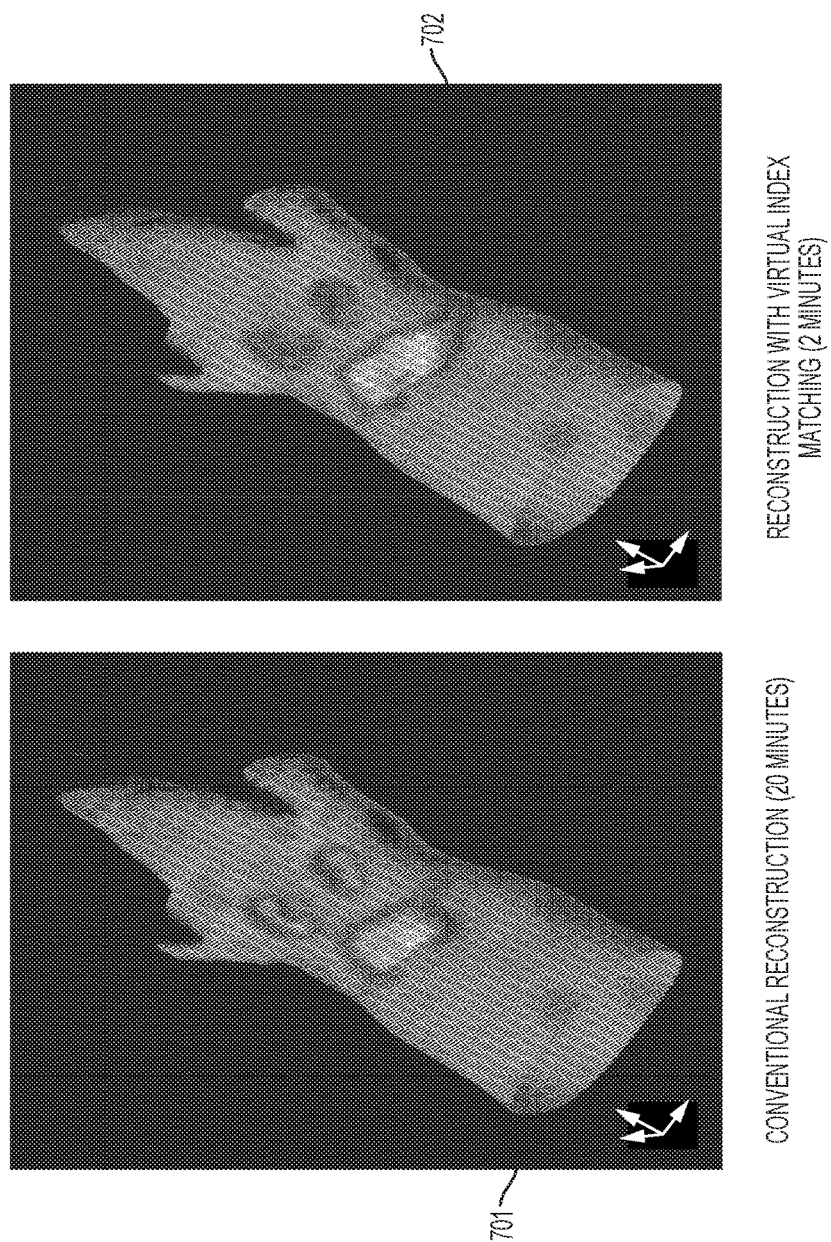
FIG. 7 depicts reconstructed 3D images of a mouse, comparing the virtual index matching approach, according to an illustrative embodiment of the invention, with conventional reconstruction.
Figure 8:
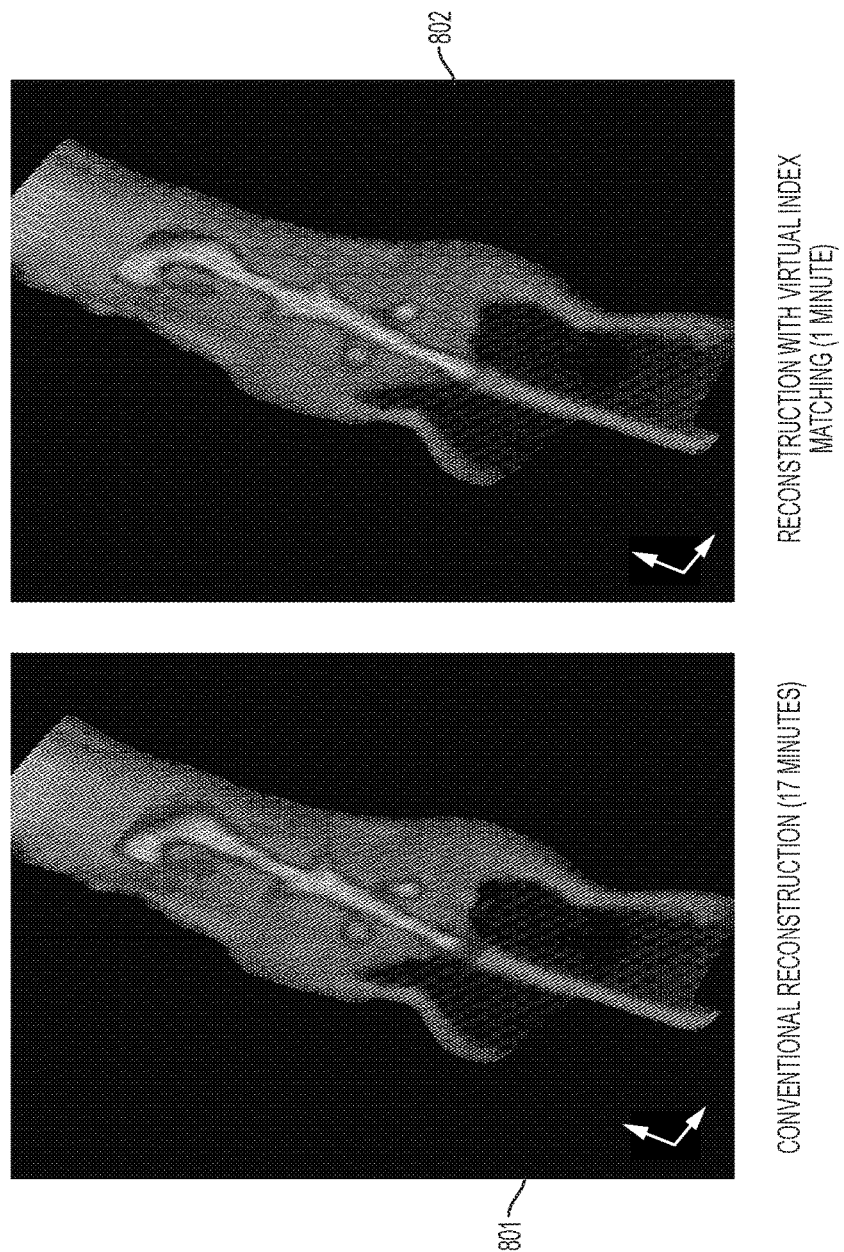
FIG. 8 depicts reconstructed 3D images of a mouse, comparing the virtual index matching approach, according to an illustrative embodiment of the invention, with conventional reconstruction.
Figure 9:
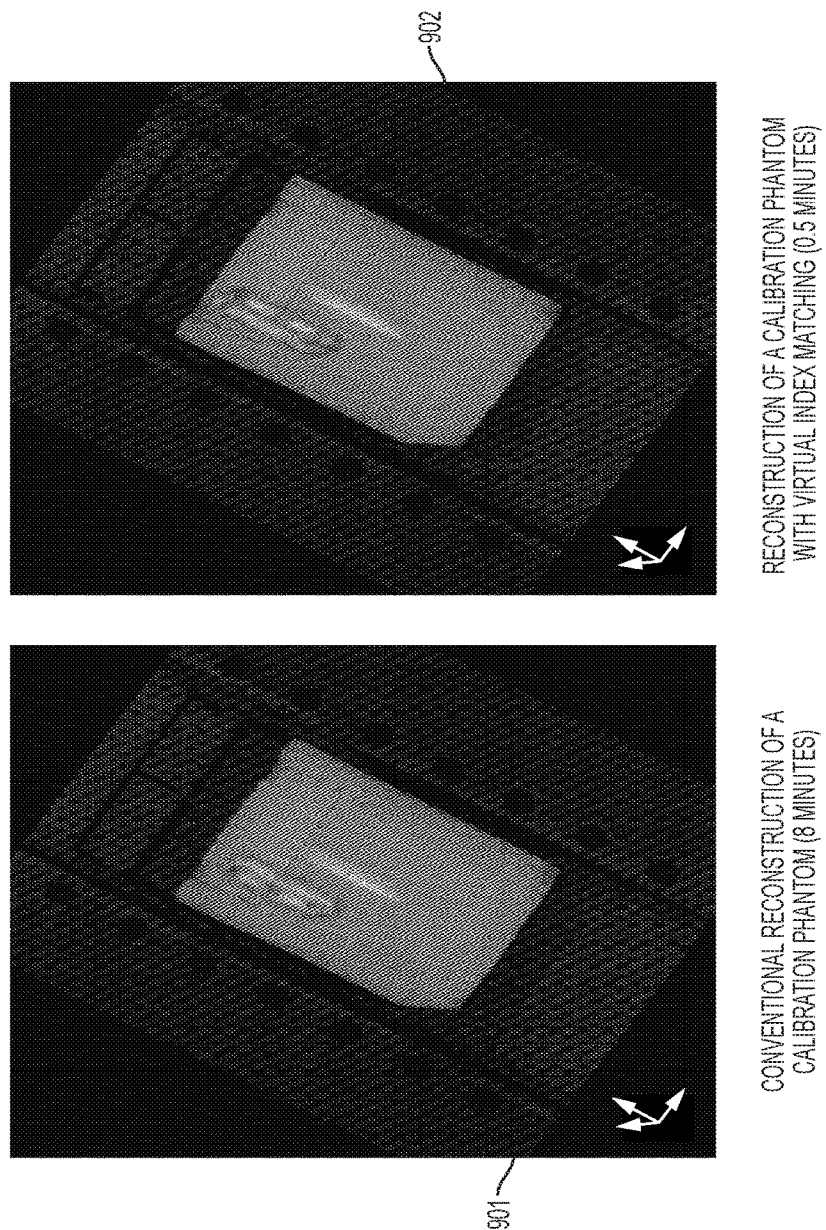
FIG. 9 depicts reconstructed 3D images of a calibration phantom, comparing the index matching approach, according to an illustrative embodiment of the invention, with conventional reconstruction.

Illustrative examples of tomographic reconstructions performed with the benefit of the virtual index-matching approach are shown in FIGS. 7-9. FIG. 7 shows examples of reconstructions performed on adult female Nu/Nu mice injected with the 4T1 model of breast cancer in the mammary fat pads. Mammary tumors and liver are imaged with the agent ProSense 750 on the FMT 2500 Imaging System (both commercially available through VisEn Medical, Bedford, Mass.). Reconstructed images of mice in panel 701 are obtained with conventional tomographic reconstruction techniques at a computational time of 20 minutes. Reconstructed images of mice in panel 702 are obtained with the virtual index-matching approach at a computational time of 2 minutes.

FIG. 8 shows examples of reconstructions performed on female, adult, nude mice. Spine and hips are imaged with the agent OsteoSense 680 using the FMT 2500 Imaging System (both commercially available through VisEn Medical, Bedford, Mass.). Reconstructed images of mice in panel 801 are obtained with conventional tomographic reconstruction techniques at a computational time of 17 minutes. Reconstructed images of mice in panel 802 are obtained with the virtual index-matching approach at a computational time of 1 minute.

FIG. 9 shows examples of reconstructions performed in vitro on phantoms using free dye and the FMT2500 (commercially available through VisEn Medical, Bedford, Mass.). Reconstructed images of the phantom in panel 901 are obtained with conventional tomographic reconstruction techniques at a computational time of 8 minutes. Reconstructed images of the phantom in panel 902 are obtained with the virtual index-matching approach at a computational time of 0.5 minutes. The images of FIGS. 7-9 depict the improved, shorter computational time of the virtual index-matching approach compared to conventional reconstruction techniques.

In certain embodiments, the methods of the present invention are useful with optical imaging modalities and measurement techniques including, but not limited to: endoscopy; fluorescence endoscopy; luminescence imaging; bioluminescence tomography, time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

Commercially available systems that can be used to employ the systems and methods described herein include, but are not limited to, the following: eXplore Optix™, Optix® and SoftScan® (ART—Advanced Research Technologies, Canada), NightOWL® II LB (Berthold Technologies, Germany), NanoSPECT™, NanoPET/CT™ and HiSPECT® (Bioscan, Washington, D.C.), Photon Imager™, Beta Imager™, Micro Imager, Gamma Imager (Biospace Lab, France), Maestro® FLEX and Nuance® FLEX (Cambridge Research and Instrumentation—Cri®, Woburn, Mass.), LightSpeed™, BrightSpeed™ and MR Signa® Series, eXplore Series, Triumph™ (GE® Healthcare, United Kingdom), Kodak® In-Vivo Imaging FX Systems, Kodak® In-Vivo Multispectral Imaging FX Systems and Kodak® Image Station 4000 series (KODAK® and Carestream®, Rochester, N.Y.), Aquacosmos® (Hamamatsu, Japan), CTLM® and LILA Imaging Systems (Imaging Diagnostic Systems—IMDS, Plantation, Fla.), Odyssey® Infrared Imaging System, Pearl® Imager (LI-COR, Lincoln, Nebr.), IMRIS® Neuro System (IMRIS®, Canada), Cellvizio® (Mauna Kea Technologies, France), SPY® and SPY®-TMR Systems, HELIOS™, LUNA™, PINPOINT®, and OPTTX® Imaging Systems (Novadaq, Canada), DYNOT Imaging System (NIRx, Glen Head, New York), OV100 and IV100 (Olympus Corporation, Japan), Lumazone® (Photometrics, Tucson, Ariz.), and IVIS® Systems, IVIS® 3D, IVIS® Kinetics, IVIS® Spectrum and IVIS® Lumina (Xenogen®, Alamaeda, Calif. and Caliper® Life Sciences, Hopkinton, Mass.), iBox® (UVP, Upland, Ca), and VisEn FMT-1, VisEn FMT 1500™, and VisEn FMT 2500™ LX (VisEn™ Medical, Bedford, Mass.).

Systems of the invention may include a computer which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

In certain embodiments, the invention features an in vivo imaging method for selectively imaging a subject containing two or more imaging probes simultaneously, wherein two or more imaging probes are administered to a subject, either at the same time or sequentially. The imaging probes can be any combination of optical or other imaging agents. A single imaging agent may serve as both an optical and other imaging modality agent, e.g., dual imaging agent. The method therefore allows the recording of multiple biological processes, functions or targets. The methods of the invention can be used to determine a number of indicia, including tracking the localization of the imaging probes in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

In certain embodiments, this invention can be used with other imaging approaches such as the use of devices including but not limited to various scopes (microscopes, endoscopes), catheters and optical imaging equipment, for example computer based hardware for tomographic presentations.

The invention can be used to help a physician, surgeon, or other medical personnel to identify and characterize areas of disease, such as arthritis, cancers, metastases or vulnerable or unstable plaque, to distinguish diseased and normal tissue, such as detecting tumor margins that are difficult to detect.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. The methods of the invention can also be used in prognosis of a disease or disease condition. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone, including metastases), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants). The methods of the invention can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The methods and compositions of the invention can also be used in identification and evaluation of cell death, injury, apoptosis, necrosis, hypoxia and angiogenesis. The methods and compositions of the invention can also be used in for monitoring trafficking and localization of certain cell types, including T-cells, tumor cells, immune cells, stem cells, and other cell types. In particular, this method may be used to monitor cell based therapies. The methods and compositions of the invention can also be used as part of photodynamic therapy, including imaging, photoactivation and therapy monitoring.

In certain embodiments, the systems and methods described herein can be used to image endogenous fluorescence in a subject. For example, a gene encoding a fluorescent protein, such as green, red or infrared fluorescent protein, can be included adjacent to a gene of interest that is to be expressed in an animal or human subject using standard gene therapy and transgenic techniques. The expression of the gene of interest can be determined indirectly by imaging the fluorescent protein. If this protein is expressed, then the gene of interest has also been expressed. Fluorescence properties of endogenous fluorescent proteins are described in Giepmans et al., *Science*, 312: 217-224, 2006; Shaner et al., *Nature Methods* 2:905-909, 2005; and Zhang et al., *Nat. Rev. Mol. Biol.* 3: 906-918, 2002; Ai et al., *Biochemistry* 46:5904-5910, 2007; Shaner et al., *Nat. Biotech* 22:1567-1572, 2004; Campbell et al., *Proc. Nat. Acad. Sci.* 99:7877-7882, 2002; Heikal et al. *Proc. Nat. Acad. Sci.* 97:11996-12001, 2000; Baird et al., *Proc. Nat. Acad. Sci.* 97:11984-11989, 2000; Tsien, *Ann. Rev. Biochem.* 67:509-44, 1998; Heim et al., *Curr. Biol.* 6:178-182, 1996; Cubitt et al., *Trends Biochem Sci.* 11:448-455, 1995; Heim et al., *Proc. Nat. Acad. Sci* 91:12501-12504, 1994; the relevant text incorporated by reference herein.

Imaging Probes

The imaging system and method can be used with a number of different imaging probes, for example, (1) probes that become activated after target contact (e.g., binding or interaction) (Weissleder et al., *Nature Biotech.*, 17:375-378, 1999; Bremer et al., *Nature Med.*, 7:743-748, 2001; Campo et al., *Photochem. Photobiol.* 83:958-965, 2007); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001;

Ballou et al. *Biotechnol. Prog.* 13:649-658, 1997; and Neri et al., *Nature Biotech.* 15:1271-1275, 1997); (5) quantum dot or nanoparticle-based imaging probes, including multivalent imaging probes, and fluorescent quantum dots such as amine T2MP EviTags® (Evident Technologies) or Qdot® Nanocrystals (Invitrogen™); (6) non-specific imaging probes e.g., indocyanine green, AngioSense® (VisEn Medical); (7) labeled cells (e.g., such as cells labeled using exogenous fluorophores such as VivoTag™ 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this invention, the imaging probes can be administered systemically or locally by injecting an imaging probe or by topical or other local administration routes, such as "spraying". Furthermore, imaging probes used in the application of this invention can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In general, fluorescent quantum dots used in the practice of this invention are nanocrystals containing several atoms of a semiconductor material (including but not limited to those containing cadmium and selenium, sulfide, or tellurium; zinc sulfide, indium-antimony, lead selenide, gallium arsenide, and silica or ormosil), which have been coated with zinc sulfide to improve the properties of the fluorescent agents.

In particular, molecular imaging probes are a preferred type of imaging probe. A molecular imaging probe is a probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, optical imaging probes have excitation and emission wavelengths in the red and near infrared spectrum in the range 550-1300 or 400-1300 nm or about 440 and about 1100 nm, between about 550 and about 800 nm, between about 600 and about 900 nm. Use of this portion of the electromagnetic spectrum maximizes tissue penetration and minimizes absorption by physiologically abundant absorbers such as hemoglobin (<650 nm) and water (>1200 nm). Optical imaging probes with excitation and emission wavelengths in other spectrums, such as the visible and ultraviolet light spectrum, can also be employed in the methods of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060 B1, WO 98/47538, WO 00/16810, EP 1 113 822 B1, WO 01/43781, EP 1 237 583 A1, WO 03/074091, EP 1 480 683 B1, WO 06/072580, EP 1 833 513 A1, EP 1 679 082 A1WO 97/40104, WO 99/51702, WO 01/21624, and EP 1 065 250 A1; and Tetrahedron Letters 41, 9185-88 (2000); all of the above incorporated by reference herein.

Exemplary fluorochromes for optical imaging probes include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-5680, VivoTag™-S750 (VIsEN Medical); Dy677, Dy682, Dy752 and Dy780 (Dyomics®); DyLight® 547, and/or DyLight® 647 (Pierce); HiLyte Fluor™ 647, HiLyte Fluor™ 680, and HiLyte Fluor™ 750 (AnaSpec®); IRDye® 800CW, IRDye® 800RS, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health).

Calibration for Concentration Mapping

The systems and methods described herein allow in vivo quantification of fluorescent agents in an animal subject. The systems can accurately reconstruct the concentration of fluorescent agents as a function of location within the animal subject. Numerical computation of the distribution of fluorescent agents produces results that are dependent on the photochemical properties of the fluorescent agents as conjugated with biologically relevant probes. Specifically, the product of the quantum yield and absorption cross-section, or extinction coefficient, are included as numerical factors in the computational result, thereby masking the actual fluorochrome concentration. A priori estimation of these photochemical properties from first principles and application of such estimates to a tomographic reconstruction of in vivo fluorescence is unreliable and prone to error. Thus, there is a need for a method to account for these photochemical properties empirically and in vivo, in order to yield accurate quantification and allocation of fluorescent agent concentration.

The calibration method enables accurate quantification of FMT tomographic reconstructions of the distribution of fluorescent agent. The method involves the measurement by FMT of a known amount of fluorescent agent in solution (for example VivoTag680 or VivoTag750, VisEn Medical, Bedford, Mass.), injected into a phantom. This phantom can either be a synthetic material designed to match the optical properties of animal tissue and containing a cavity designed to hold the fluorescent agent, or it can be a container holding fluorescent agent that is in turn placed inside an animal cadaver. Phantom material may, for example, consist of an optically clear polyester resin (TAP Plastics, Dublin, Calif.) with a dispersion of Titanium Dioxide (TiO2, Sigma-Aldrich, St. Louis, Mo.) and ink to adjust the optical scattering and optical absorption properties of the phantom to those of biological tissue. Phantoms may be molded, machined or fabricated to any desired geometry or aspect ratio. In one embodiment, phantoms are molded to dimensions representative of small animal anatomies (such as thicknesses spanning a range of 13-25 mm) and machined with internal hollow cavities to accommodate fluorescent agents with dimensions representative of disease-related lesions in various animal models (such as tumor sizes in the range of 50-500 µL). These hollow cavities may be located at depths representative of various disease manifestations, from close to the surface (for subcutaneous disease models) to full depth within the phantom. The concentration of fluorescent agent in solution is measured in vitro, for example using spectrophotometry instrumentation such as the devices provided by Varian (Palo Alto, Calif.), before dispensing a known volume of the solution into the phantom. A complete FMT dataset of the phantom is then acquired, and the raw data are tomographically reconstructed. A region of interest (ROI) analysis is performed on the reconstructed distribution of fluorescent agent. The values in this ROI are then numerically scaled to match the known amount of fluorescent agent that had been dispensed into the phantom. Finally, this scale factor is applied to future reconstructions to convert the raw result of the tomographic reconstruction into a physically meaningful concentration of fluorescent agent. Scale factors can be generated to account for the photochemical properties of different fluorescent agents, such as ProSense680, OsteoSense750 and others (VisEn Medical, Bedford, Mass.). This calibration process may be repeated several times per agent to increase the statistical robustness of the calibration and decrease the impact of operator variability, batch to batch agent variability, and other sources of error. It is also possible to generate a single, scalar scale factor or a scale factor function mapping to an entire range of concentrations, as appropriate. The scale factor may also be a function of depth within the subject being scanned or of other physical properties of the subject. These functional scale factors may also be combined to produce a scale factor function with multiple parameters. Calibration of phantoms using the virtual index-matching approach is depicted in FIG. 9, panel 902.

The following references, and all other references identified herein, are incorporated by reference herein in their entirety: Arridge, S. R., H. Dehghani, et al. (2000), "The finite element model for the propagation of light in scattering media: a direct method for domains with nonscattering regions," *Med* 27(1): 252-64; Hielscher, A. H., R. E. Alcouffe, et al. (1998), "Comparison of finite-difference transport and diffusion calculations for photon migration in homogeneous and heterogeneous tissues," *Phys. Med. Biol.* 43: 1285-1302; Markel, V. A. and J. C. Schotland (2001), "Inverse scattering for the diffusion equation with general boundary conditions," *Phys Rev E* 64(3 Pt 2): 035601; Markel, V. A. and J. C. Schotland (2004), "Symmetries, inversion formulas, and image reconstruction for optical tomography," *Phys Rev E Stat Nonlin Soft Matter Phys* 70(5 Pt 2): 056616; Ntziachristos, V., J. Ripoll, et al. (2005), "Looking and listening to light: the evolution of whole-body photonic imaging," *Nat Biotechnol* 23(3): 313-20; Ripoll, J., M. Nieto-Vesperinas, et al. (2002), "Fast analytical approximation for arbitrary geometries in diffuse optical tomography," *Optics Letters* 27(7): 527-529; Ripoll, J., V. Ntziachristos, et al. (2001), "The Kirchhoff Approximation for diffusive waves," *Phys. Rev. E* 64: 051917: 1-8.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A fluorescence molecular tomography imaging system comprising:
    an excitation light source;
    an optical imaging apparatus configured to direct light from the excitation light source into a subject at a plurality of locations;
    a detector configured to detect at multiple locations fluorescent light emanating from a region of the subject; and
    a memory having instructions stored thereon, wherein the instructions, when executed by a processor, cause the processor to:
        using data corresponding to the detected fluorescent light, establish a forward model of (a) excitation light propagation from the excitation light source to the region of the subject and of (b) fluorescent light propagation from the region of the subject to the detector, such that light propagation is modeled as if there is no discontinuity in refraction index at a surface of the subject, wherein
            one or more virtual-matching transformations are applied to the data corresponding to the detected fluorescent light to account for a refractive index discontinuity at the surface of the subject, wherein application of the one or more virtual-matching transformations to the data corresponding to the detected fluorescent light results in transformed data, wherein each of the one or more virtual-matching transformations is derived from a boundary condition which relates measured flux to surface-dependent average intensity and expresses average intensity that would be present in absence of the surface; and
        obtain a tomographic representation of the region of the subject using the forward model in combination with the transformed data.

2. The system of claim 1, wherein:
    in the forward model, the excitation light source is represented in real space, and the detected fluorescent light is represented in frequency space; and
    the tomographic representation of the region of the subject is a representation in real space.

3. The system of claim 1, wherein:
    the detector comprises a detector array;
    establishing the forward model comprises establishing a plurality of virtual detectors, wherein the plurality of virtual detectors conform to an imposed geometry different from an arrangement of the detector array; and the forward model simulates light propagation from the region of the subject to the plurality of virtual detectors.

4. The system of claim 3, wherein the imposed geometry is a planar array.

5. The system of claim 1, wherein:
the detector is configured to detect excitation light emanating from the subject; and
establishing the forward model comprises establishing the forward model using both data corresponding to the detected excitation light and the data corresponding to the detected fluorescent light.

6. The system of claim 5, wherein, establishing the forward model comprises applying one or more virtual-matching transformations to the data corresponding to the detected excitation light.

7. The system of claim 5, wherein the excitation light source is represented in real space, the detected excitation light is represented in frequency space, the detected fluorescent light is represented in frequency space, and the tomographic representation of the region of the subject is a representation in real space.

8. The system of claim 5, wherein:
the detected fluorescent light is emitted from a probe within the region of the subject; and
the forward model models (a) excitation light propagation from the excitation light source to the probe and (b) emitted fluorescent light propagation from the probe to the detector.

9. The system of claim 8, wherein establishing the forward model comprises using a Born approximation to express an intensity of the detected fluorescent light emitted from the probe, wherein the intensity of the detected fluorescent light has spatially-varying concentration within the region of the subject.

10. The system of claim 5, wherein establishing the forward model comprises normalizing the intensity of the detected fluorescent light using an intensity of spatially-corresponding detected excitation light.

11. The system of claim 5, wherein the forward model represents the detected excitation light and the detected fluorescent light in corresponding virtually-matched expressions.

12. The system of claim 5, wherein the excitation light comprises at least one member selected from a group consisting of continuous wave light, time-resolved light, and intensity modulated light.

13. The system of claim 5, wherein the detected excitation light is detected after passing through at least a portion of the subject.

14. The system of claim 1, comprising a scanner configured to direct light into the subject at a plurality of locations, thereby defining a plurality of source locations.

15. The system of claim 14, wherein the plurality of source locations are non-uniformly spaced.

16. The system of claim 1, wherein establishing the forward model comprises using an experimental measurement of surface flux distribution.

17. The system of claim 1, wherein the forward model comprises a weight matrix of normalized elements.

18. The system of claim 1, wherein the surface of the subject and the detector are separated in part by free space.

19. The system of claim 1, wherein the tomographic representation displays a quantitative concentration of a fluorophore within the subject in three dimensions.

20. The system of claim 1, wherein establishing the forward model comprises processing the data corresponding to the detected fluorescent light to detect and compensate for an effect of optical heterogeneity in the medium.

21. A method of tomographic imaging comprising:
directing excitation light from an excitation light source into a subject at a plurality of locations to transilluminate through or reflect from at least a portion of a region of the subject containing a probe previously administered to the subject;
detecting at multiple locations excitation light transmitted through or reflected from the region of the subject;
detecting fluorescent light emitted from the probe;
establishing, by a processor of a computing device, using data corresponding to the detected fluorescent light and data corresponding to the detected excitation light, a forward model of excitation light propagation of (a) the excitation light source to the probe and of (b) emission light propagation from the probe to a detector, wherein establishing the forward model comprises
applying one or more virtual-matching transformations both to the data corresponding to the detected fluorescent light and the data corresponding to the detected excitation light, wherein
the virtual-matching transformations account for a refractive index discontinuity at a surface of the subject, and
application of the one or more virtual-matching transformations results in transformed data, wherein each of the one or more virtual-matching transformations is derived from a boundary condition which relates measured flux to surface-dependent average intensity and expresses average intensity that would be present in absence of the surface, and
normalizing an intensity of the detected fluorescent light using an intensity of spatially-corresponding detected excitation light, wherein
the forward model is modeled as if (a) the subject is surrounded by an infinite and homogeneous diffusive medium and (b) there is no discontinuity in refraction index at the surface of the subject; and
obtaining, by the processor, using the forward model in combination with the transformed data, a tomographic representation of the region of the subject.

22. The method of claim 21, wherein the tomographic representation comprises a map of concentration of the probe within the region of the subject.

23. The method of claim 21, wherein the probe is an endogenous probe.

24. The method of claim 21, wherein the probe comprises a member selected from a group consisting of a molecular probe, a fluorescent molecular probe, an activatable fluorescent probe, an enzyme-activatable fluorescent probe, a targeted fluorescent probe, a near-infrared fluorescent molecular probe, a fluorescent protein, a fluorescent biomolecule, a non-specific fluorescent probe, quantum dots, a receptor-targeted near-infrared fluorochrome, an antibody- or antibody-like targeted near-infrared fluorochrome, a wavelength-shifting beacon, a multi-color fluorescence probe, and a lanthanide metal-ligand probe.

25. The method of claim 21, wherein the probe comprises a fluorochrome attached to a delivery vehicle comprising one or more of a polymer, a dendrimer, a protein, a carbohydrate, a lipid sphere, and a nanoparticle.

26. The method of claim 21, wherein:
the probe comprises a plurality of probes, wherein each probe of the plurality of probes has an optically distinguishable fluorescent emission wavelength in relation to the remaining probes of the plurality of probes;
detecting the fluorescent light comprises detecting, for each probe of the plurality of probes, fluorescent light, wherein the data corresponding to the detected fluorescent light comprises respective data corresponding to each probe of the plurality of probes; and
obtaining the tomographic representation comprises obtaining one or more tomographic representations.

27. The method of claim 21, wherein:
at least (a) directing the excitation light, (b) detecting the excitation light, (c) detecting the fluorescent light, (d) establishing the forward model, and (e) obtaining the tomographic representation are repeated to obtain a plurality of tomographic representations as a function of time; and
the method comprises using the plurality of tomographic representations to monitor kinetics of at least one of (i) a distribution of the probe and (ii) an activation of the probe within the region of the subject.

28. The method of claim 21, wherein the excitation light comprises one or more wavelengths of a natural tissue chromophore.

29. The method of claim 21, wherein the tomographic representation comprises a map showing quantity of the probe in three dimensions.

30. The method of claim 21, wherein the tomographic representation indicates an area of disease within the region of the subject.

31. The method of claim 21, wherein the tomographic representation indicates an area of arthritis, cancer, metastasis, plaque, or a combination of two or more of the foregoing, within the region of the subject.

32. The method of claim 21, wherein the tomographic representation indicates a boundary of a tumor within the region of the subject.

33. The method of claim 21, further comprising determining an effect of the probe on the region within the subject using the tomographic representation.

34. The method of claim 21, wherein the tomographic representation comprises one or more images, and wherein the method further comprises storing the one or more images, displaying the one or more images, or both storing and displaying the one or more images.

35. The method of claim 21, further comprising a step of detecting or monitoring a cellular abnormality or disease using the tomographic representation, wherein the cellular abnormality or disease comprises at least one member from selected from a group consisting of inflammation, cancer, cardiovascular disease, respiratory disease, dermatologic disease, ophthalmic disease, infectious disease, immunologic disease, central nervous system disease, inherited disease, metabolic disease, environmental disease, bone-related disease, neurodegenerative disease, and surgery-related complication.

36. The method of claim 21, wherein the probe comprises an endogenous fluorophore that is encoded by a gene within the subject.

37. The method of claim 36, further comprising a step of determining expression of the gene encoding the fluorophore using the tomographic representation.

38. The method of claim 36, wherein the endogenous fluorophore is a fluorescent protein or biomolecule.

39. The method of claim 21, wherein the tomographic representation comprises a three-dimensional tomographic image, the method comprising:

combining the three-dimensional tomographic image with at least one of magnetic resonance data, x-ray computed tomography data, bioluminescence tomography data, spectroscopy data, ultrasound data, single photon emission tomography data, and positron emission tomography imaging data.

40. The method of claim 21, wherein establishing the forward model comprises processing the data corresponding to the detected fluorescent light to detect and compensate for an effect of optical heterogeneity in the medium.

41. A non-transitory machine-readable medium having instructions stored thereon, wherein the instructions, when executed by a processor, cause the processor to:
establish a forward model of (a) excitation light propagation from an excitation light source to a probe within a region of a subject and of (b) emission light propagation from the probe to a detector using both data corresponding to detected fluorescent light from the probe and data corresponding to detected excitation light transmitted through or reflected from the region of the subject, wherein establishing the forward model comprises
applying one or more virtual-matching transformations to (i) the data corresponding to the detected fluorescent light and (ii) the data corresponding to the detected excitation light, wherein the one or more virtual-matching transformations are configured to account for a refractive index discontinuity at a surface of the subject, wherein each of the one or more virtual-matching transformations is derived from a boundary condition which relates measured flux to surface-dependent average intensity and expresses average intensity that would be present in absence of the surface, and
normalizing an intensity of the detected fluorescent light using an intensity of spatially-corresponding detected excitation light, wherein
the forward model is modeled as if the subject is surrounded by an infinite and homogeneous diffusive medium and there is no discontinuity in refraction index at the surface of the subject; and
using the forward model, obtain a tomographic representation of the region of the subject.

42. The machine-readable medium of claim 41, wherein:
the excitation light source is represented in real space;
the detected fluorescent light and the detected excitation light are each represented in frequency space; and
the tomographic representation of the region of the subject is a representation in real space.

43. A diffuse optical tomography imaging system comprising:
one or more illumination sources;
an optical imaging apparatus configured to direct light from the at least one illumination source into a subject at a plurality of locations;
a detector configured to detect at multiple locations light emanating from the subject to obtain a first measurement and a second measurement, wherein
the first measurement is a reference measurement, and
the second measurement corresponds to absorption of at least a portion of the light as it passes through a region of the subject,
wherein the reference measurement does not reflect all of said absorption;

a processor; and a memory having instructions stored thereon, wherein the instructions, when executed by the processor, cause the processor to:

using data corresponding to the first measurement and data corresponding to the second measurement, establish a forward model of (a) light propagation from at least one illumination source of the one or more illumination sources to a light-absorbing region within the subject and of (b) light propagation from the region within the subject to the detector, wherein establishing the forward model comprises applying one or more virtual-matching transformations to at least one of the data corresponding to the first measurement and the data corresponding to the second measurement, wherein the one or more virtual-matching transformations are configured to account for a refractive index discontinuity at a surface of the subject, wherein each of the one or more virtual-matching transformations is derived from a boundary condition which relates measured flux to surface-dependent average intensity and expresses average intensity that would be present in absence of the surface, wherein the forward model is modeled as if the subject is surrounded by an infinite and homogeneous diffusive medium and there is no discontinuity in refraction index at the surface of the subject; and using the forward model, obtain a tomographic representation of the region of the subject.

44. The system of claim 43, wherein the one or more illumination sources comprise at least two illumination sources, wherein each illumination source of the at least two illumination sources has a different wavelength than a respective wavelength of the remaining illumination sources.

45. The system of claim 44, wherein the respective wavelengths of the at least two illumination sources comprise a wavelength below an isosbestic point of an oxy-hemoglobin (HbO) and a deoxy-hemoglobin (Hb), and a wavelength above the isosbestic point.

46. The system of claim 43, wherein the light is configured to transilluminate the subject.

* * * * *